US012691089B2

(12) United States Patent
Donovan et al.

(10) Patent No.: US 12,691,089 B2
(45) Date of Patent: Jul. 28, 2026

(54) STABLE LEVOTHYROXINE COMPOSITIONS IN APROTIC POLAR SOLVENTS

(71) Applicant: Xeris Pharmaceuticals, Inc., Chicago, IL (US)

(72) Inventors: Martin Donovan, El Paso, TX (US); Wendy Hu, San Diego, CA (US); Richard Fitch, Chicago, IL (US); Steven Prestrelski, San Diego, CA (US)

(73) Assignee: Xeris Pharmaceuticals, Inc., Chicago, IL (US)

( * ) Notice: Subject to any disclaimer, the term of this patent is extended or adjusted under 35 U.S.C. 154(b) by 0 days.

(21) Appl. No.: 19/401,887

(22) Filed: Nov. 26, 2025

(65) Prior Publication Data

US 2026/0076932 A1     Mar. 19, 2026

Related U.S. Application Data

(60) Division of application No. 18/934,749, filed on Nov. 1, 2024, now Pat. No. 12,514,837, which is a continuation of application No. 18/490,218, filed on Oct. 19, 2023.

(60) Provisional application No. 63/380,090, filed on Oct. 19, 2022.

(51) Int. Cl.
| | |
|---|---|
| *A01N 43/00* | (2006.01) |
| *A01N 43/46* | (2006.01) |
| *A61K 9/00* | (2006.01) |
| *A61K 9/08* | (2006.01) |
| *A61K 31/198* | (2006.01) |
| *A61K 31/55* | (2006.01) |
| *A61K 47/02* | (2006.01) |
| *A61K 47/20* | (2006.01) |
| *A61K 47/26* | (2006.01) |
| *A61K 47/34* | (2017.01) |

(52) U.S. Cl.
CPC .......... *A61K 31/198* (2013.01); *A61K 9/0019* (2013.01); *A61K 9/08* (2013.01); *A61K 47/02* (2013.01); *A61K 47/20* (2013.01); *A61K 47/26* (2013.01); *A61K 47/34* (2013.01)

(58) Field of Classification Search
CPC ...... A61K 9/08; A61K 31/7088; A61K 47/12; A61K 47/186; A61K 47/20; A61K 47/24; A61K 2039/05; A61P 17/06
See application file for complete search history.

(56) References Cited

U.S. PATENT DOCUMENTS

| | | |
|---|---|---|
| 4,727,041 A | 2/1988 | Aroonsakul |
| 5,065,747 A | 11/1991 | Bercu |
| 9,339,545 B2 | 5/2016 | Prestrelski et al. |
| 9,649,264 B2 | 5/2017 | Ferrari et al. |
| 9,649,364 B2 | 5/2017 | Prestrelski et al. |
| 10,485,850 B2 | 11/2019 | Prestrelski et al. |
| 11,020,403 B2 | 6/2021 | Prestrelski et al. |
| 2018/0271948 A1 | 9/2018 | Prestrelski et al. |
| 2020/0376083 A1 | 12/2020 | Donovan et al. |
| 2021/0059967 A1 | 3/2021 | Parikh et al. |
| 2021/0401945 A1 | 12/2021 | Cassavaugh et al. |
| 2024/0148678 A1 | 5/2024 | Donovan et al. |
| 2024/0148680 A1 | 5/2024 | Donovan et al. |
| 2025/0057797 A1 | 2/2025 | Donovan et al. |

FOREIGN PATENT DOCUMENTS

| | | |
|---|---|---|
| DE | 10024752 A1 | 11/2001 |
| WO | WO-2017013591 A1 | 1/2017 |
| WO | WO-2018222922 A1 | 12/2018 |

OTHER PUBLICATIONS

Boguszewski, C.L., "Glucagon Stimulation Test: Has Its Time Come?" Endocrine 57(3):361-363, Humana Press, United States (Sep. 2017).

Boye, K., et al., "Patients' preferences for Once-Daily Oral versus Once-Weekly Injectable Diabetes Medications: The REVISE Study," Diabetes Obes Metab 23(2):508-519, Wiley-Blackwell Publishing Ltd., United Kingdom (Feb. 2021).

Hepp, Z., et al., "Adherence to Thyroid Hormone Replacement Therapy: A Retrospective, Claims Database Analysis," Curr Med Res Opin 34(9):1673-1678, Taylor and Francis Ltd., United Kingdom (Sep. 2018).

International Search Report and Written Opinion for International Application No. PCT/US2023/077271, European Patent Office, Netherlands, mailed on Feb. 1, 2024, 11 pages.

International Search Report and Written Opinion for International Application No. PCT/US2023/077272, European Patent Office, Netherlands, mailed on Feb. 1, 2024, 11 pages.

Ledeti, I., et al., "Stability and Compatibility Studies of Levothyroxine Sodium in Solid Binary Systems—Instrumental Screening," Pharmaceutics 12(1):58, Multidisciplinary Digital Publishing Institute, Switzerland (Jan. 2020).

(Continued)

*Primary Examiner* — Layla Soroush

(74) *Attorney, Agent, or Firm* — STERNE, KESSLER, GOLDSTEIN & FOX P.L.L.C.

(57) ABSTRACT

The present invention concerns the use of aprotic polar solvents and an ionization stabilizing agent to prepare stable therapeutic formulations of levothyroxine by dissolving levothyroxine in an aprotic polar solvent system that can then be used to treat, prevent, and/or diagnose certain diseases and disorders in humans and veterinary animals by administration of the formulation thereto. In certain embodiments, the invention is directed to formulations comprising levothyroxine, and optionally one or more additional therapeutic agents, dissolved in an aprotic polar solvent system, such as a DMSO/water admixture comprising at least one ionization stabilizing excipient in a concentration sufficient to impart physical and chemical stability to the therapeutic agent. The invention also provides methods of use of such formulations in treating, preventing, and/or diagnosing diseases and disorders, and methods of manufacturing such formulations.

13 Claims, 22 Drawing Sheets

(56) References Cited

OTHER PUBLICATIONS

Meyer, L.M., et al., "Stability and Consistency of Compounded Oral Liquid Levothyroxine Formulations," J Am Pharm Assoc 60(6):e168-e172, American Pharmacists Association, United States (Nov.-Dec. 2020).

Sanchez, J.C., "Theoretical Aspects of Levothyroxine: Bioavailability and Drug Stability," MOJ Bioequiv Availab 5(1):53-54, MedCrave, United States (Feb. 2018).

Weeda, E.R., et al., "Medication Adherence to Injectable Glucagon-Like Peptide-1 (GLP-1) Receptor Agonists Dosed Once Weekly vs Once Daily in Patients with Type 2 Diabetes: A Meta-Analysis," Int J Clin Pract 75(9):e14060, Wiley-Hindawi, United Kingdom (Sep. 2021).

Yuen, K.C.J., "Glucagon Stimulation Testing in Assessing for Adult Growth Hormone Deficiency: Current Status and Future Perspectives," ISRN Endocrinol 2011:608056, International Scholarly Research Network, United States (2011).

Picazo, J., ed., *Glucagon in Gastroenterology*, Chapters 3-7, pp. 39-120, MTP Press Ltd., Lancaster, England (1979).

Makadia, H. K., et al., "Poly Lactic-co-Glycolic Acid (PLGA) as Biodegradable Controlled Drug Delivery Carrier," Polymers (Basel), 3(3): 1377-1397, United States (Sep. 2011).

Abbreviations:  d = day; PK = pharmacokinetics; PO = per oral; SC = subcutaneous; wo = washout

FIG. 14A

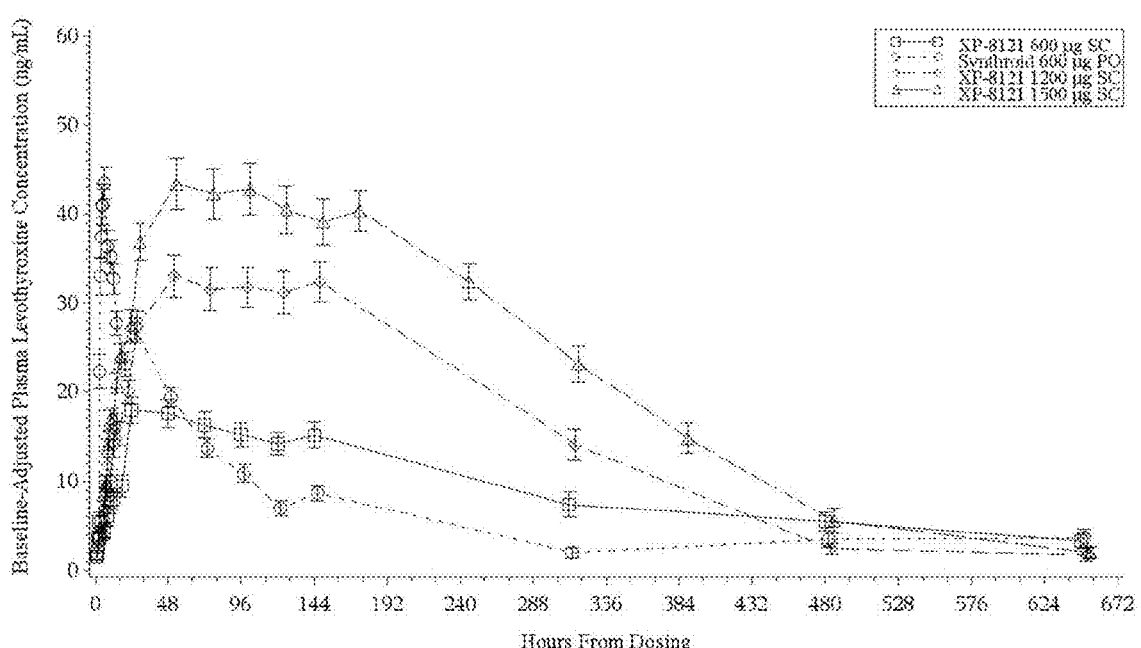

Synthroid 600 ng PO, XP-8121 1200 ng SC, XP-8121 1500 ng SC are shifted to the right for ease of reading.
PE ~ Pharmacokinetic; SC ~ Subcutaneous; PO ~ Oral administration; SE ~ Standard error
Program: /CA34173/sas_prg/pksas/adam_meangraph_T4.sas 02SEP2022 10:17

FIG. 14B

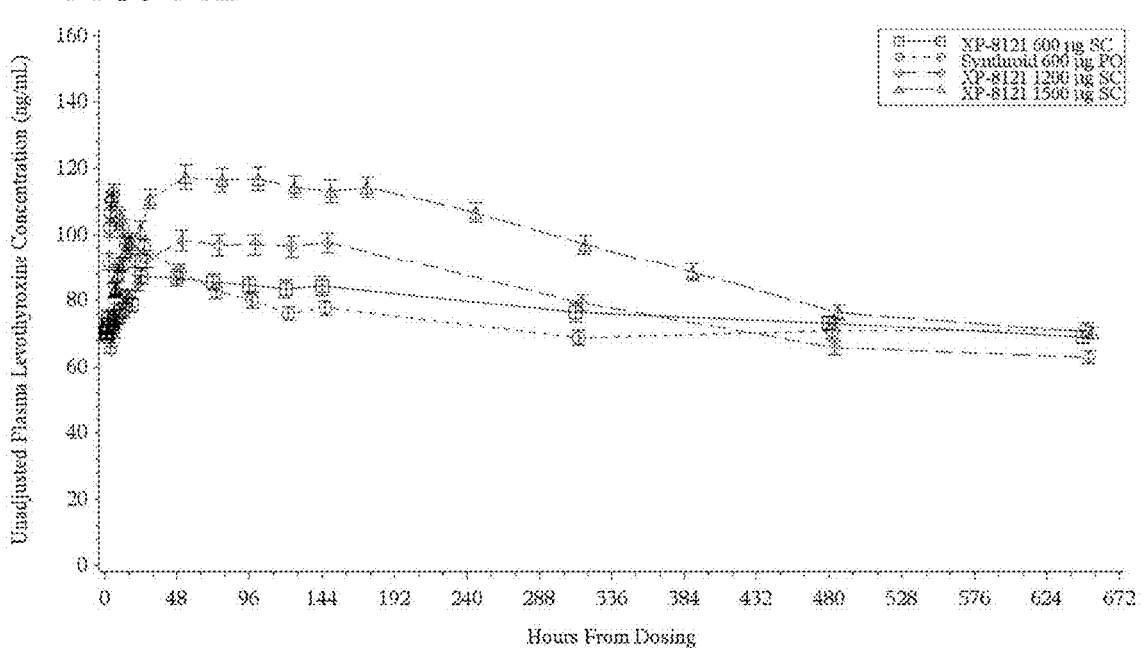

Synthroid 600 ng PO, XP-8121 1200 ng SC, XP-8121 1500 ng SC are shifted to the right for ease of reading.
PE ~ Pharmacokinetic; SC ~ Subcutaneous; PO ~ Oral administration; SE ~ Standard error
Program: /CA34173/sas_prg/pksas/adam_meangraph_T4.sas 02SEP2022 10:17

Median (Range) Levothyroxine T$_{max}$

Mean (SD) Baseline-Adjusted Levothyroxine Half-Life

Mean (SD) Baseline-Adjusted Levothyroxine C$_{max}$

Synthroid PO 600 ug (N=29)
XP-8121 SC 600 ug (N=29)
XP-8121 SC 1200 ug (N=28)
XP-8121 SC 1500 ug (N=30)

Mean (SD) Baseline-Adjusted Levothryoxine AUC$_{last}$

Synthroid PO 600 ug (N=29)
XP-8121 SC 600 ug (N=29)
XP-8121 SC 1200 ug (N=28)
XP-8121 SC 1500 ug (N=30)

1

STABLE LEVOTHYROXINE COMPOSITIONS IN APROTIC POLAR SOLVENTS

CROSS-REFERENCE TO RELATED APPLICATIONS AND INCORPORATION BY REFERENCE

This application is a divisional of U.S. application Ser. No. 18/934,749, filed Nov. 1, 2024, which is a continuation of U.S. patent application Ser. No. 18/490,218, filed Oct. 19, 2023, which claims the benefit of U.S. Provisional Appl. No. 63/380,090, filed Oct. 19, 2022, which are hereby incorporated by reference in their entireties.

BACKGROUND OF THE INVENTION

A. Field of the Invention

The present invention is in the field of medical and pharmaceutical arts. Certain embodiments relate generally to therapeutic aprotic solvent formulations comprising one or more active pharmaceutical ingredients that may be used as therapeutic formulations in treating, preventing, and/or diagnosing diseases, disorders and medical conditions in mammals, particularly humans. In particular, the invention concerns the use of aprotic polar solvents, water, and at least one ionization stabilizing agent to prepare stable therapeutic formulations of a variety of active pharmaceutical ingredients, such as levothyroxine, by dissolving a therapeutic agent (active pharmaceutical ingredient), such as levothyroxine, in an aprotic polar solvent system to produce stable therapeutic formulations useful in treating, preventing and/or diagnosing diseases or physical disorders in humans and veterinary animals.

B. Description of Related Art

Oral levothyroxine has been the standard of care treatment for hypothyroidism for many years, and it is one of the most prescribed medicines in the United States, generating more than 100 million prescriptions per year. While generally safe and effective, oral levothyroxine presents several challenges to hypothyroid patients taking this chronic medication. These challenges may include inadequate absorption of levothyroxine in the GI tract as well as patient compliance with the chronic daily treatment regimen, resulting in suboptimal control of TSH levels. It has been estimated that up to 30-60% of hypothyroid patients may not be well-controlled. More specifically, TSH control may be negatively impacted by the adverse effects of food, concomitant medications, and GI comorbidities on the absorption of oral levothyroxine in the GI tract. In addition, TSH control may be negatively impacted by poor patient compliance with the chronic daily regimen of oral levothyroxine, especially since the effects of skipping doses do not immediately result in the apparent negative health consequences.

A retrospective analysis of insurance claims data from a commercially insured population during the period of Jan. 1, 2000-Mar. 31, 2016 (Hepp, Z. et al., Curr. Med. Res. Opin. 34(9): 1673-1678, DOI: 10.1080/03007995.2018.148629 (2018)) found that 51.9% of patients with hypothyroidism were non-adherent at 12 months post-initiation on therapy (non-adherence defined as the proportion of days covered [PDC] being <80% and PDC defined as the percentage of unique days an individual received the levothyroxine formulation in the period of interest). The long-term health complications of hypothyroidism may include goiter, an increased risk of heart disease and heart failure, depression, slowed mental functioning, peripheral neuropathy, infertility, birth defects, developmental and intellectual problems in infants, and, in rare cases, the life-threatening myxedema coma.

Multiple branded and generic presentations of oral levothyroxine exist, including solid and liquid presentations with varying excipients, however, all fundamentally pass through the GI tract and are prescribed for once-daily use. An injectable presentation of levothyroxine also exists but is an IV injection that is indicated only for the treatment of myxedema coma/crisis.

A recent study in patients with diabetes showed that an injectable formulation of levothyroxine, dosed once weekly, was associated with an 11% lower risk of non-adherence compared to a once daily injectable (Weeda, E. R. et al., Int. J. Clin. Pract. (2021) February 1:e14060. doi: 10.1111/ijcp.14060 (Epub ahead of print; PMID: 33527605)). Another recent study in patients with diabetes found that ~50% of patients preferred a once weekly injectable to a once daily oral when specific administration requirements for the oral were taken into consideration (Boye, K. et al., Diabetes Obes Metab. 23(2):508-519 (2021), doi: 10.1111/dom.14244). These findings suggest that injectable aqueous formulations of levothyroxine for treatment of hypothyroidism might be preferable to the once-daily oral levothyroxine (e.g., Synthroid® (levothyroxine sodium; Abbvie, North Chicago, IL)) typically prescribed to patients with hypothyroidism. However, stable and bioactive aqueous formulations of levothyroxine have proven difficult to produce, given the poor solubility of levothyroxine in aqueous solvents and the rapid degradation of the molecule in aqueous solutions, which often require the presence of carefully selected mixtures of formulation excipients to overcome (see, e.g., Ledeţi, I. et al., Pharmaceutics 12:58 (2020), doi 10.3390/pharmaceutics12010058; Sanchez, J. C., MOJ Bioequiv. Bioavail. 5(1):53-54 (2018); Meyer et al., J. Am. Pharm. Assn. 60:e168-e172 (2020), doi 10.1016/j.japh.2020.05.014).

Thus, there is a need in the art for a stable, ready-to-use formulation of levothyroxine intended for once-weekly (and even less frequent) patient self-administration in the outpatient setting for the treatment of hypothyroidism and associated physical disorders and diseases. Such formulations would offer several advantages over those that are currently commercially available, including injection of the formulation in a way that bypasses the gastrointestinal tract (e.g., subcutaneously), thereby avoiding absorption challenges that exist with currently used oral formulations of levothyroxine, and potentially improving the patient experience and patient compliance relative to a daily oral regimen. In addition, such formulations could provide improved solubility of levothyroxine and longer-term storage stability of the resulting formulation, improving the economic profile of these therapeutic formulations relative to other commercial offerings.

BRIEF SUMMARY OF THE INVENTION

Embodiments described herein provide formulations comprising a variety of pharmaceutical ingredients, such as levothyroxine, meeting the above-noted needs in the art. In additional embodiments, the invention also provides methods of producing such formulations, and methods of use of the formulations in treating, preventing and/or diagnosing a variety of diseases, disorders and physical conditions in humans and veterinary animals.

Embodiments described herein provide storage stable compositions (formulations) comprising one or more therapeutically active ingredient (e.g., one or more active pharmaceutical ingredient), suitably a therapeutic peptide or small molecule such as levothyroxine. In other embodiments, the present invention provides methods of making such storage stable therapeutic formulations. In additional embodiments, the invention provides methods of using the storage stable formulations of the invention in methods of treating, preventing and/or diagnosing certain diseases, physical disorders or conditions in animals, including veterinary animals and humans, suffering from or predisposed to such diseases, physical disorders or conditions.

In certain exemplary embodiments, the present invention provides a storage-stable levothyroxine formulation that is useful in treating and/or preventing hypothyroidism, particularly severe hypothyroidism such as myxedema or myxedema coma/crisis, as well as being useful as an adjunct to certain other therapeutic procedures.

Such formulations suitably leverage the same nonaqueous formulation technology (XeriSol™; Xeris Pharmaceuticals, Inc., Chicago, IL) as an immediate release glucagon rescue product that is currently commercially available (Gvoke®; Xeris Pharmaceuticals) to address the stability and solubility challenges with certain small molecule or peptide-containing aqueous compositions. Such storage stable formulations of the present invention are clear, ready-to-use, non-aqueous solutions prior to injection. Upon administration, for example subcutaneously, the small molecule or peptide therapeutic forms a depot due to poor solubility under physiological conditions, promoting the gradual release of the therapeutic molecule(s) into the bloodstream and resulting in improved bioavailability, pharmacokinetics, and in some situations sustained release, of the therapeutic molecule(s) compared to orally administered or immediate-release parenterally administered compositions.

Thus, in certain embodiments the present invention provides a therapeutic formulation comprising (a) at least one therapeutic agent, (b) at least one ionization stabilizing excipient, and (c) an aprotic polar solvent, particularly wherein the formulation is storage stable for at least two years at refrigerated conditions (e.g., 2° C.-8° C.), and wherein the formulation, when administered to a patient, results in the presence of therapeutic levels of the therapeutic agent in the blood of the patient for an extended period of time relative to an immediate release formulation comprising the same therapeutic agent. In certain such embodiments, the therapeutic agent is a small molecule or a salt thereof, which may be any small molecule therapeutic. Examples of such small molecule therapeutics include but are not limited to levothyroxine, sumatriptan, ketorolac and ondansetron. In other such embodiments, the therapeutic agent is a peptide such as a glucagon peptide, glucagon analog, glucagon mimetic, or salt thereof.

At least one ionization stabilizing excipient is dissolved in the aprotic solvent in an amount to stabilize the ionization of the therapeutic agent. In certain aspects, the ionization stabilizing excipient is at a concentration of 0.01 mM to less than 200 mM. The ionization stabilizing excipient can be a proton donating (e.g., acid) and/or proton accepting (e.g., base) component. The ionization stabilizing excipient can be, but is not limited to, a mineral acid. In certain embodiments, the mineral acid can be selected from hydrochloric acid, sulfuric acid, nitric acid and phosphoric acid. The ionization stabilizing excipient may also be an organic acid (acids having a carboxylic acid-COOH functional group). Non-limiting examples of organic acids include acetic acid, citric acid, malic acid, lactic acid, and amino acids. In certain aspects, the aprotic solvent is DMSO. In particular aspects, the ionization stabilizing excipient is a mineral acid, particularly sulfuric acid or hydrochloric acid, and the aprotic solvent is DMSO.

In other embodiments, the invention provides methods of treating, ameliorating or preventing a disease, physical condition or disorder in a patient, such as a veterinary animal or a human, suffering from or predisposed to such disease, physical condition or disorder. Suitable such methods according to certain aspects of the invention comprise introducing an effective amount of a storage stable formulation of the invention into a patient in need thereof in a manner suitable to promote the release of the therapeutic compound from the formulation into the bloodstream of the patient. In certain such embodiments, the formulation is introduced into the subject via parenteral administration, for example via injection (which may be a subcutaneous, intradermal or intramuscular injection) or infusion (which may be intravenous, or which may be accomplished by pump infusion, e.g., by continuous or bolus pump infusion, or a combination thereof). In certain aspects, the invention provides methods of treating or preventing hypothyroidism in a human by administering to the human a storage stable levothyroxine formulation of the present invention. In certain other aspects, the invention provides methods of treating or preventing hypoglycemia in a human by administering to the human a storage stable glucagon formulation of the present invention.

In additional embodiments, the present invention provides methods of producing a storage stable therapeutic formulation, said method comprising mixing at least one ionization stabilizing excipient, an aprotic polar solvent, and at least one therapeutic agent, thereby forming a storage stable therapeutic formulation that, when administered to a patient, results in the presence of therapeutic levels of said therapeutic agent in the blood of said patient, in some cases for an extended period of time relative to an immediate release formulation comprising the same therapeutic agent.

In additional aspects, the invention provides methods of diagnosing a disease or physical disorder in a human patient by introducing an effective amount of one of the storage stable formulations of the invention into a patient suffering from or predisposed to, or suspected of suffering from or being predisposed to, a disease or disorder, as an adjunct to a diagnostic test and conducting the diagnostic test on the patient. Suitable formulations useful in accordance with this aspect of the invention include those described elsewhere herein, particularly storage stable glucagon formulations of the invention. Such diagnostic methods can be used for diagnosing a variety of diseases, physical disorders and physical conditions, including but not limited to Alzheimer's Disease, a growth hormone deficiency and a gastrointestinal disorder. In aspects where the methods are used in the diagnosis of a gastrointestinal disorder, the diagnostic test suitably is a radiology test of the gastrointestinal tract of said patient. In carrying out these diagnostic methods of the invention, the storage stable therapeutic formulation can be introduced into the patient by any parenteral route, particularly orally, intragastrically, intravenously, intramuscularly, subcutaneously or intradermally.

To produce the storage stable therapeutic formulations of the invention, at least one ionization stabilizing excipient can be dissolved in the aprotic solvent in an amount sufficient to stabilize the ionization of the therapeutic agent.

Suitable such ionization stabilizing excipients (including but not limited to mineral acids), and desirable concentrations for inclusion in the formulations of the invention, include those described in detail elsewhere herein.

The formulations can further include a preservative at less than 10, 5, or 3% w/v. In certain aspects, the preservative is benzyl alcohol.

The formulations can further include one or more disaccharides at less than 10, 5, or 3% w/v. In certain embodiments, the disaccharide is trehalose dihydrate at about 5.5% w/v.

The formulations can further include one or more sugar alcohols at less than 10, 5 or 3% w/v. In certain embodiments, the sugar alcohol is mannitol at about 2.9% (w/v).

In certain embodiments, the formulation can have freezing point of about 10° C. or less, for example about 10° C., about 5° C., about 0° C., or less than about 0° C., e.g., less than –20° C., or between –50° C. to –70° C.

Therapeutic molecules typically require an optimal or beneficial ionization profile in order to exhibit prolonged stability when solubilized in an aprotic polar solvent system. Maintaining the beneficial ionization profile of a therapeutic molecule dissolved in an aprotic polar solvent system can be achieved by using at least one ionization stabilizing excipient. In certain aspects, the therapeutic molecule is not required to be previously dried from a buffered aqueous solution prior to reconstitution in the aprotic polar solvent system. The ability to use existing (e.g., commercially available) devices and the ability to circumvent the need for drying a therapeutic molecule (e.g., a peptide) from a buffered aqueous solution can save considerable time and cost throughout the various product development stages.

Stable solutions of a therapeutic agent(s) solubilized in non-aqueous aprotic polar solvents (e.g., DMSO) can be prepared by adding a specific amount of a compound, or combination of compounds, that function as an ionization stabilizing excipient. Without wishing to be bound by theory, it is believed that the ionization stabilizing excipient can act as a proton source (e.g., a molecule that can donate a proton to the therapeutic molecule) in the aprotic polar solvent system that may protonate the ionogenic groups on the therapeutic molecule such that the therapeutic molecule possesses an ionization profile having an improved physical and chemical stability in the aprotic polar solvent system. Alternatively, the ionization stabilizing excipient can act as a proton sink (e.g., a molecule or moiety that can accept/ remove a proton from the therapeutic molecule) such that the therapeutic molecule possesses an ionization profile having an improved physical and chemical stability in the aprotic polar solvent system.

Certain embodiments are directed to a formulation comprising an ionization stabilizing excipient at a concentration of at least, at most, or about 0.01, 0.1, 0.5, 1, 10, or 50 mM to 10, 50, 75, 100, 500, 1000 mM, or up to the solubility limit of the ionization stabilizing excipient in the aprotic polar solvent system. In certain aspects, the ionization stabilizing excipient concentration is between about 0.1 mM to about 100 mM, particularly about 1 mM to about 35 mM, e.g., about 1 mM, about 2 mM, about 3 mM, about 4 mM, about 5 mM, about 6 mM, about 7 mM, about 8 mM, about 9 mM, about 10 mM, about 15 mM, about 20 mM, about 25 mM, about 30 mM, about 32 mM and about 35 mM, and all ranges and concentrations therebetween. In certain embodiments, the ionization stabilizing excipient may be a suitable mineral acid, such as hydrochloric acid, sulfuric acid, nitric acid and the like. In certain aspects, the ionization stabilizing excipient may be an organic acid, such as an amino acid, amino acid derivative, or the salt of an amino acid or amino acid derivative (examples include glycine, trimethylglycine (betaine), glycine hydrochloride, and trimethylglycine (betaine) hydrochloride). In a further aspect, the amino acid can be glycine or the amino acid derivative trimethylglycine. In certain aspects, a peptide is less than 150, 100, 75, 50, or 25 amino acids. In further aspects, the aprotic solvent system comprises DMSO. The aprotic solvent can be deoxygenated, e.g., deoxygenated DMSO. In certain embodiments, the formulation may be prepared by first adding the ionization stabilizing excipient to the aprotic polar solvent system, followed by addition of the therapeutic molecule. Alternatively, the therapeutic molecule may initially be solubilized in the aprotic polar solvent system followed by addition of the ionization stabilizing excipient. In a further aspect, the ionization stabilizing excipient and the therapeutic molecule may be solubilized simultaneously in the aprotic polar solvent system. In certain aspects, the therapeutic agent is glucagon, a glucagon analogue, or salt thereof.

Other embodiments of the present invention are directed to methods of stably formulating a therapeutic agent (e.g., a peptide or a small molecule) comprising: (a) calculating or determining the appropriate ionization stabilizing excipient (e.g. proton concentration) needed to achieve a stabilizing ionization profile of a target therapeutic agent (e.g., a peptide(s) or small molecule(s)) in an aprotic polar solvent system; (b) mixing at least one ionization stabilizing excipient with the aprotic polar solvent system to attain an appropriate ionization environment that provides the ionization profile determined in (a); and (c) solubilizing the target therapeutic agent(s) in the aprotic solvent having an appropriate environment to physically and chemically stabilize the therapeutic agent. In certain non-limiting aspects, the therapeutic agent is chemically or physically stable for at least or about 0.25, 0.5, 1, 2, 3, 4, or 5 years, and more preferably about 0.25 to about 3 years, and even more preferably at least about 6 months to about 2 years, at room temperature, at refrigerated temperatures (e.g., about 2° C. to about 10° C. or about 2° C., about 3° C., about 4° C., about 5° C., about 6° C., about 7° C., about 8° C., about 9° C. or about 10° C.), or at sub-zero temperatures (e.g., about –4° C. to about –80° C., or about –4° C., about –10° C., about 15° C., about –20° C., about –25° C., about –40° C., about –45° C., about –50° C., about –60° C., about –70° C., or about –80° C.). In certain aspects, the dissolution of the therapeutic agent and the addition of the ionization stabilizing excipient to the aprotic polar solvent system can be done in any order or concurrently. The present inventors have found, however, that to maximize the dissolution, stability and/or bioactivity of some therapeutic agents, e.g., levothyroxine, it is preferable that the ionization stabilizing excipient be admixed with the aprotic polar solvent first followed by dissolution of the therapeutic agent in the admixture. However, other formulations of the invention can be prepared by first dissolving the therapeutic agent in the aprotic polar solvent first followed shortly thereafter (e.g., within about 5 minutes) by addition of the ionization stabilizing excipient to the solution, or the ionization stabilizing excipient and the therapeutic agent can be added to or dissolved in an aprotic polar solvent system concurrently. One or more additional formulation components (e.g., a sustained release modifying agent (e.g., a polymeric compound such as poly(lactic-coglycolic acid) or PLGA; see U.S. Patent Publication No. US 2021/ 0401945 A1, which is incorporated herein by reference in its entirety), preservatives, surfactants, polysaccharides, sugar alcohols, etc.) may be incorporated into the formulation either prior to or following addition of the therapeutic agent.

The concentration of the therapeutic agent and/or ionization stabilizing excipient added to the solution can be between 0.01, 0.1, 1, 10, 100, 1000 mM, or up to its solubility limit, including all values and ranges there between, as described in more detail elsewhere herein. In certain aspects, the aprotic polar solvent system is deoxygenated. In a further aspect the aprotic polar solvent in the solvent system comprises, consists essentially of, or consists of DMSO or deoxygenated DMSO.

In a further aspect of the present invention, there is disclosed a method for treating or preventing a condition, disease, disorder, etc. comprising administering to a subject in need thereof a formulation(s) of the present invention in an amount effective to treat or prevent the condition, disease, disorder, etc. Any suitable dosage of a therapeutic agent (e.g., protein, peptide, or small molecule) may be administered in the methods of the present invention. The dosage administered will, of course, vary depending upon known factors, such as the pharmacodynamic characteristics of the particular compound, salt, or combination; the age, health, or weight of the subject; the nature and extent of symptoms; the metabolic characteristics of the drug and patient, the kind of concurrent treatment; the frequency of treatment; or the effect desired. In certain aspects, hypothyroidism can be treated or prevented by administering a formulation described herein comprising an effective amount of levothyroxine. In other aspects hypoglycemia can be treated by administering a formulation described herein comprising an effective amount of glucagon.

The stable formulations described herein are useful for the parenteral injection of any therapeutic agent (protein, peptide, and/or small molecule) that has limited or poor stability or solubility in an aqueous environment. In certain aspects, a formulation as described herein is provided in as an injectable formulation. The injectable formulation can be administered into the epidermal, dermal, subcutaneous or intramuscular layer of a patient. In certain aspects, the formulations are administered via injection into the skin, particularly intradermally or subcutaneously.

Definitions

The term "container," "reservoir," "infusion set," "pump," "formulation-flow path," "fluid flow path," etc. should be interpreted as interchangeable and equivalent being these components will be in direct contact with the formulations being administered or stored with potential to interact with the components and their surfaces. The terms imply any and all components that the formulation will contact during storage (e.g., pump reservoir) and delivery (e.g., fluid flow path in pump and the infusion set when connected in series to a pump). The term "infusion set" as used herein may be interpreted to include both internal infusion sets (i.e., those contained within patch pumps) as well as complete tubing systems that connect a pump to the pump user and are generally external to the pump. In certain configurations, external infusion sets include a cannula (e.g., for subcutaneous administration), an adhesive mount, quick-disconnect, and a pump cartridge connector (for example, a Luer-type connector).

The terms "formulation" and "composition" may be used interchangeably herein, and as used herein refer to an admixture of at least two components to produce a preparation comprising all of those components, some of those components, or complexes or reaction mixtures or reaction resulting from the admixture of the components.

The term "dissolution" as used herein refers to a process by which a material(s) in a gas, solid, or liquid state becomes a solute(s), a dissolved component(s), of a solvent, forming a solution of the gas, liquid, or solid in the solvent. In certain aspects, a therapeutic agent or an excipient, e.g., an ionization stabilizing excipient or a sustained release modifier or other component, is present in an amount up to its solubility limited or is fully solubilized. The term "dissolve" refers to a gas, liquid, or solid becoming incorporated into a solvent to form a solution The term "elastomer" as used herein refers to a natural or synthetic polymer having elastic properties. The terms "elastomer" and "rubber" may be used interchangeably herein.

The term "excipient" as used herein refers to a natural or synthetic substance formulated alongside the active or therapeutic ingredient (an ingredient that is not the active ingredient) of a medication, included for the purpose of stabilization, bulking, or to confer a therapeutic enhancement on the active ingredient in the final dosage form, such as facilitating drug absorption, reducing viscosity, enhancing or reducing aqueous or non-aqueous solubility, adjusting tonicity, mitigating injection site discomfort, depressing the freezing point, or enhancing stability. Excipients can also be useful in the manufacturing process, to aid in the handling of the active substance concerned such as by facilitating powder flowability or non-stick properties, in addition to aiding in vitro stability such as prevention of denaturation or aggregation over the expected shelf life.

"Small molecule drugs" in the context of the present invention are biologically active compounds (and salts thereof) that can bring about a desired, beneficial, and/or pharmacological effect on a subject. These "small molecule drugs" are organic or inorganic compounds. Therefore, the small molecule drugs in the context of the present invention are not polymeric compounds. Typically, the small molecule drugs have a molecular weight of less than approximately 1000 Daltons. Certain small molecule drugs are "moisture sensitive" in that they are increasingly unstable in the presence of water. Also, salts that can be used with the small molecule drugs are known to those skilled in the art and include salts with inorganic acids, organic acids, inorganic bases, or organic bases.

The term "therapeutic agent" or "therapeutic" encompasses proteins, peptides, small molecule drugs, and pharmaceutically acceptable salts thereof. Useful salts are known to those skilled in the art and include salts with inorganic acids, organic acids, inorganic bases, or organic bases. Therapeutic agents useful in the present invention are those protein, peptide, and small molecule compounds that affect a desired, beneficial, and often pharmacological, effect upon administration to a human or an animal, whether alone or in combination with other pharmaceutical excipients or inert ingredients.

The term "peptide" and "peptide compound" refers to amino acid or amino acid-like (peptidomimetics) polymers of up to about 200 amino acid residues bound together by amide (CONH) or other linkages. In certain aspects, a peptide can be up to 150, 100, 80, 60, 40, 20, or 10 amino acids. "Protein" and "protein compound" refer to polymers of greater than 200 amino acid residues bound together by amide linkages. Analogs, derivatives, agonists, antagonists, and pharmaceutically acceptable salts of any of the peptide or protein compounds disclosed here are included in these terms. The terms also include peptides, proteins, peptide compounds, and protein compounds that have D-amino acids, modified, derivatized, or naturally occurring amino acids in the D- or L-configuration and/or peptomimetic units as part of their structure.

"Analogue" and "analog," when referring to a peptide or protein, refers to a modified peptide or protein wherein one or more amino acid residues of the peptide or protein have been substituted by other amino acid residues, or wherein one or more amino acid residues have been deleted from the peptide or protein, or wherein one or more amino acid residues have been added to the peptide or protein, or any combination of such modifications. Such addition, deletion, or substitution of amino acid residues can take place at any point, or multiple points, along the primary structure comprising the peptide, including at the N-terminal of the peptide or protein and/or at the C-terminal of the peptide or protein.

"Derivative," in relation to a parent peptide or protein, refers to a chemically modified parent peptide or protein or an analog thereof, wherein at least one substituent is not present in the parent peptide or protein an analog thereof. One such non-limiting example is a parent peptide or protein which has been covalently modified. Typical modifications are amides, carbohydrates, alkyl groups, acyl groups, esters, pegylations and the like.

"Single-phase solution" refers to a solution prepared from a therapeutic agent that is dissolved in a solvent, or solvent system (e.g., mixture of two or more solvents (e.g. solvent and a co-solvent)), wherein the therapeutic agent is completely dissolved in the solvent or solvent system and there is no longer particulate matter visible, such that the solution can be described as optically clear. A single-phase solution may also be referred to as a "single-phase system," and is distinguished from a "two-phase system" in that the latter is comprised of particulate matter (e.g., powder) suspended in a fluid.

"Inhibiting" or "reducing" or any variation of these terms includes any measurable decrease or complete inhibition to achieve a desired result.

"Effective" or "treating" or "preventing" or any variation of these terms means adequate to accomplish a desired, expected, or intended result.

"Chemical stability," when referring to a therapeutic agent, refers to an acceptable percentage of degradation products produced by chemical pathways such as oxidation and/or hydrolysis and/or fragmentation and/or other chemical degradation pathways. In particular, a formulation of the type described herein may be considered chemically stable if no more than about 20% breakdown products are formed after at least one year of storage at the intended storage temperature of the product (e.g., refrigerated storage or subzero storage); or storage of the product at accelerated conditions (25° C./60% relative humidity) for one month, two months or preferable three months. In some embodiments, a chemically stable formulation has less than 30%, less than 25%, less than 20%, less than 15%, less than 10%, less than 5%, less than 4%, less than 3%, less than 2%, or less than 1% breakdown products formed after an extended period of storage at the intended storage temperature of the product.

"Physical stability," when referring to a therapeutic agent, refers to an acceptable percentage of aggregates (e.g., dimers, trimers and larger forms) being formed. In particular, a formulation is considered physically stable if no more than about 15% aggregates are formed after at least one year of storage at the intended storage temperature of the product (e.g., refrigerated storage, subzero storage); or storage of the product at 25° C./60% relative humidity for one month, two months, and preferably at least three months. In some embodiments, a physically stable formulation has less than less than 15%, less than 10%, less than 5%, less than 4%, less than 3%, less than 2%, or less than 1% aggregates formed after an extended period of storage at the intended storage temperature of the product.

"Stable formulation" refers to a formulation where at least about 65% of the therapeutic agents (e.g., small molecules, peptides, or salts thereof) remain chemically and physically stable after at least one month of storage at room temperature, or up to at least one year of storage at refrigerated or subzero temperatures. Particularly preferred formulations are those in which at least about 80%, 85%, 90%, 91%, 92%, 93%, 94%, 95%, 96%, 97%, 98%, or 99% chemically and physically stable therapeutic agent remains under these storage conditions. Especially preferred stable formulations are those which do not exhibit degradation after sterilizing irradiation (e.g., gamma, beta, or electron beam).

As used herein, "parenteral injection" refers to the administration of therapeutic agents (e.g., peptides or small molecules) via a route other than the alimentary canal—any administration that is not by way of the digestive tract—for example, intravenous infusion, intranasal administration, buccal administration, transdermal administration, or injection under or through one or more layers of skin or mucus membranes of an animal, such as a human. Standard parenteral injections are given into the subcutaneous, intramuscular, or intradermal tissues of an animal, e.g., a human. These deep locations are targeted because the tissue expands more easily relative to shallow dermal sites to accommodate injection volumes required to deliver most therapeutic agents, e.g., 0.1 to 3.0 cc (mL).

The term "intracutaneous" encompasses administration into the epidermal or dermal skin layers.

As used herein, the term "aprotic polar solvent" refers to a polar solvent which does not contain acidic hydrogen and thus does not act as a hydrogen bond donor. Polar aprotic solvents include, but are not limited to dimethylsulfoxide (DMSO), dimethylformamide (DMF), ethyl acetate, n-methyl pyrrolidone (NMP), dimethylacetamide (DMA), and propylene carbonate.

As used herein, the term "aprotic polar solvent system" refers to a solution wherein the solvent is a single aprotic polar solvent (for example, neat DMSO), or a mixture of two or more aprotic polar solvents (for example, a mixture of DMSO and NMP), or a mixture of at least one aprotic polar solvent with at least one other pharmaceutically acceptable solvent system. One non-limiting example would be a solvent system comprising an aprotic polar solvent (e.g., DMSO) and a protic polar solvent (e.g., propylene glycol). In additional aspects, the term "aprotic polar solvent system" refers to a solution wherein the solvent is one or more aprotic polar solvents admixed with an amount of moisture, e.g., water, at a v/v ratio of at least about 99.9% aprotic solvent to about 0.1% water, up to a v/v ratio of at least about 50% aprotic solvent to about 50% water.

As used herein, "residual moisture" may refer to the residual moisture (typically, residual water) in the drug powder following preparation by the manufacturer/supplier. Typical powders often have residual moisture contents ranging from up to 10% (w/w). When these powders are dissolved in an aprotic polar solvent system, the residual moisture in the powder is incorporated into the formulation. Additionally, the aprotic polar solvents may also contain a certain level of residual moisture. For example, a freshly opened bottle of USP-grade DMSO may contain up to 0.1% (w/w) moisture. The residual moisture is different from "added moisture," where water is intentionally added to the formulation, for example to serve as a co-solvent, or to depress the freezing point of the aprotic polar solvent system. Moisture may also be introduced into the formulation during addition of an ionization stabilizing excipient (for example, through addition of a mineral acid from an aqueous stock solution (e.g., 1 N HCl or $H_2SO_4$)), or through the addition of water (e.g., water for injection). The total moisture content (% w/w, unless otherwise stated) in a formulation immediately following preparation is due to the contributions from both the residual moisture and the added moisture. Such formulations may still be defined as "non-aqueous," which for the purposes of this disclosure encompasses formulations that comprise less than about 50% water.

As used herein, "device flow path" refers to a part of a device that can come into contact with a formulation/solution/solvent, during administering the formulation/solution/solvent to a subject using the device. In some aspects, the device can be an infusion set in series with a pump capable of parenterally administering a formulation/solution/solvent to a subject through various needles and/or tubing. In other aspects, the device can be a patch pump that is directly adhered to the patient, and which does not require the use of an external infusion set connected in series with the pump.

The term "about" or "approximately" or "substantially unchanged" are defined as being close to as understood by one of ordinary skill in the art, and in one non-limiting embodiment the terms are defined to be within 10%, preferably within 5%, more preferably within 1%, and most preferably within 0.5%. Further, "substantially non-aqueous" refers to less than 5%, 4%, 3%, 2%, 1%, or less by weight or volume of water.

"Pharmaceutically acceptable" ingredient, excipient, or component is one that is suitable for use with humans and/or animals without undue adverse side effects (such as toxicity, irritation and allergic response) commensurate with a reasonable benefit/risk ratio.

"Pharmaceutically acceptable carrier" means a pharmaceutically acceptable solvent, suspending agent, or vehicle for delivering a drug compound of the present invention to a mammal such as a human.

As used herein, an "ionization stabilizing excipient" is an excipient that establishes and/or maintains a particular ionization state for a therapeutic agent. In certain aspects, the ionization stabilizing excipient can be, or includes, a molecule that donates at least one cation, particularly at least one divalent cation, under appropriate conditions or that is a cation (particularly a divalent cation)-donating compound or source.

As used herein a "mineral acid" is an acid that is derived from one or more inorganic compounds. Accordingly, mineral acids may also be referred to as "inorganic acids." Mineral acids may be monoprotic or polyprotic (e.g., diprotic, triprotic, etc.). Non-limiting examples of mineral acids include hydrochloric acid (HCl), nitric acid ($HNO_3$), sulfuric acid ($H_2SO_4$), and phosphoric acid ($H_3PO_4$).

As used herein, a "mineral base" (which may be equally and alternatively referred to as an "inorganic base") is a base that is derived from one or more inorganic compounds. Many, but not all, inorganic bases are generally classified as "strong bases," and non-limiting examples of inorganic bases include sodium hydroxide (NaOH), potassium hydroxide (KOH), magnesium hydroxide ($Mg(OH)_2$) and calcium hydroxide ($Ca(OH)_2$).

As used herein an "organic acid" is an organic compound with acidic properties (i.e., can function as a proton source). Carboxylic acids, such as acetic acid or citric acid, are one example of organic acids. Other known examples of organic acids include, but are not limited to, alcohols, thiols, enols, phenols, and sulfonic acids. Organic acids may be monoprotic or polyprotic (e.g., diprotic, triprotic, etc.).

As used herein, an "organic base" is an organic compound with basic properties (i.e., it can function as a proton acceptor/sink). Many, but not all, organic bases contain nitrogen atoms (e.g., amines), and non-limiting examples of organic bases include amino acids (e.g., histidine, arginine, lysine), pyridine, imidazole and tromethamine. Organic bases may accept one or more protons per molecule.

"Charge profile," "charge state," "ionization," "ionization state," and "ionization profile" may be used interchangeably and refer to the ionization state due to protonation and/or deprotonation of the peptide's ionogenic groups.

As used herein, a "co-formulation" is a formulation that contains two or more therapeutic agents dissolved in an aprotic polar solvent system. The therapeutic agents may belong to the same class (for example, a co-formulation comprising two or more therapeutic peptides, such as insulin and pramlintide, or glucagon and GLP-1), or the therapeutic agents may belong to different classes (for example a co-formulation comprising one or more therapeutic small molecules and one or more therapeutic peptide molecules, such as GLP-1 and lisofylline).

The use of the word "a" or "an" when used in conjunction with the term "comprising" in the claims and/or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 3A: 0 mM $H_2SO_4$; FIG. 3B: 2 mM $H_2SO_4$; FIG. 3C: 6 mM $H_2SO_4$; FIG. 3D: 8 mM $H_2SO_4$; FIG. 3E: 10 mM $H_2SO_4$.

FIG. 4A: 0 mM $H_2SO_4$; FIG. 4B: 2 mM $H_2SO_4$; FIG. 4C: 6 mM $H_2SO_4$; FIG. 4D: 8 mM $H_2SO_4$; FIG. 4E: 10 mM $H_2SO_4$.

FIGS. 14A-14B are a pair of line graphs showing mean baseline-adjusted plasma levothyroxine concentration in human subjects in the XP-8121-108 study, dosed with a 10 mg/mL levothyroxine formulation of the present invention (XP-8121) subcutaneously (SC) at 600 µg, 1200 µg or 1500 µg, vs. 600 µg of Synthroid® administered orally (PO). Results are plotted on a linear scale (FIG. 14A) or a semi-logarithmic scale (FIG. 14B).

DETAILED DESCRIPTION OF THE INVENTION

Figure 1A:
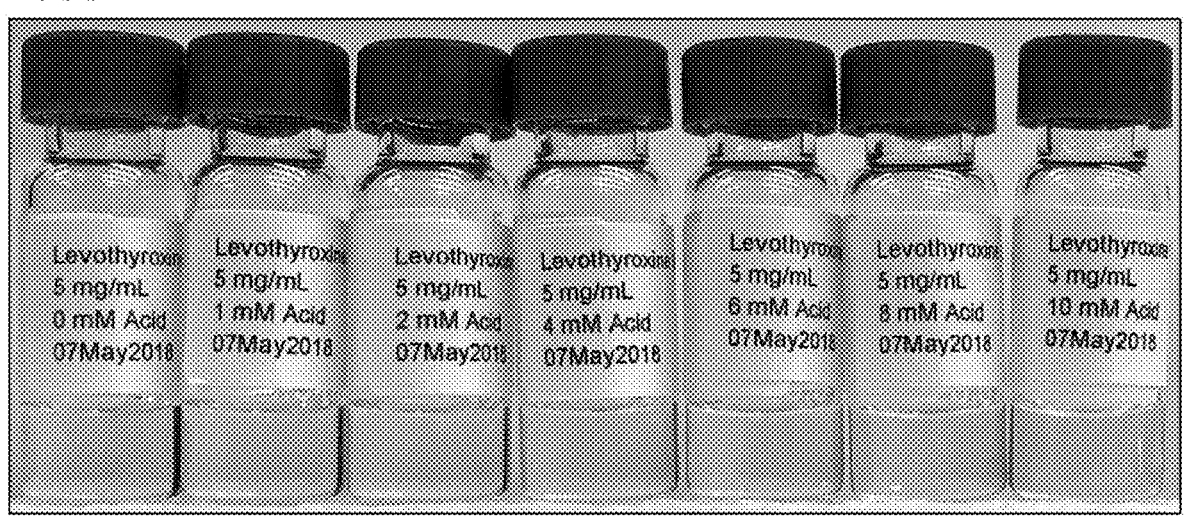
FIGS. 1A-1B are a series of photographs, showing the color of 5 mg/ml levothyroxine (sodium salt) formulations in DMSO with various concentrations of acid ($H_2SO_4$), shortly after preparation (FIG. 1A) or stored at 45° C. for 9 days (FIG. 1B).

When prepared as aqueous solutions, standard small molecule, peptide, and protein molecules may be susceptible to multiple physical and chemical degradative pathways. For many of these therapeutic molecules, degradation pathways that are catalyzed, mediated, and/or promoted by water (e.g., hydrolysis, racemization, deamidation) cannot be avoided and consequently the molecule cannot be adequately stabilized. Accordingly, many therapeutic agents cannot be prepared as stable solutions for parenteral injection and are instead prepared as powders that are reconstituted immediately prior to use.

To address the physical and/or chemical instability that many therapeutic molecules exhibit in water, formulations may be prepared wherein the therapeutic agent is dissolved in a biocompatible non-aqueous liquid, such as an aprotic polar solvent (e.g., DMSO). Previous non-aqueous formulations are at least partially based on the premise that limiting the moisture content of the formulation promotes physical and chemical stability by inhibiting water-mediated degradation pathways. Many of these known formulations limit the moisture content to at most 10% (w/w).

The use of aprotic polar solvents to prepare non-aqueous therapeutic formulations to inhibit many common degradation pathways, particularly those involving water, can significantly improve the stability of the solubilized or dissolved therapeutic molecule(s). However, problems still remain with the compositions and methods disclosed in the art. In particular, direct dissolution of a therapeutic molecule in an aprotic polar solvent is not a suitable approach for preparing stable compositions of most therapeutic molecules. Various therapeutics when solubilized directly in DMSO, for example levothyroxine at a concentration of 5 mg/mL, will discolor and form degradation products within one day of storage even in refrigeration. For a composition comprising only levothyroxine and DMSO, 5 mg/mL corresponds to approximately 0.45% (w/w) of the levothyroxine, indicating that at even relatively low concentrations, direct dissolution in an aprotic polar solvent system is by itself incapable of preventing degradation and/or gelation of a therapeutic molecule. Moreover, therapeutic molecules that may not be prone to chemical degradation in an aprotic polar solvent system may nonetheless form insoluble aggregates be when solubilized directly in an aprotic polar solvent system.

Without wishing to be bound by theory, it is thought that in order to exhibit enhanced or optimal stability and solubility when formulated in an aprotic polar solvent system, a therapeutic molecule may require a specific ionization profile. The ionization profile is the charge state acquired via protonation and/or deprotonation of the therapeutic molecule's ionogenic groups, imparting an overall positive, negative, or neutral charge state to the molecule. For example, protonation of the ionogenic amino acid residues (e.g., arginine, lysine, aspartic acid, glutamic acid) comprising a therapeutic peptide may confer an overall positive charge on the molecules in solution. Alternatively, deprotonation of ionogenic amino acid residues may confer an overall negative charge on the molecules in solution. For the non-limiting examples used herein, protonated (i.e., positively charged) molecules will be described, although the deprotonation of ionogenic amino acid residues in therapeutic peptide molecules is also considered to be within the scope of the present invention. In such embodiments, the relatively long-range electrostatic repulsions between positively charged API molecules may inhibit the shorter-range hydrophobic interactions that can result in physical instability (e.g., precipitation, aggregation and/or gelation). Thus, in the absence of sufficient protonation (i.e., an optimal or beneficial ionization profile), therapeutic molecules dissolved in an aprotic polar solvent system may be physically unstable and lead to the formation of soluble and/or insoluble aggregates or other degradation products. Accordingly, it may be necessary to include at least one excipient in a sufficient concentration to function as an ionization stabilizing agent that is capable of imparting the ionization profile for improved physical and/or chemical stability to the active agent in the aprotic polar solvent system. The appropriate concentration of the ionization stabilizing excipient(s) to be added to the solution depends on several factors including, but not limited to, the chemical structure of the ionization stabilizing excipient, the chemical structure of the active agent(s), the concentration of the active(s), the solvent system used, the presence of co-solvents, and the presence of additional excipients or formulation components and their respective concentrations.

Certain compositions and methods are designed to establish an optimal ionization profile for therapeutic molecules before they are solubilized in an aprotic polar solvent system. For example, a peptide powder from a supplier/manufacturer is initially dissolved in a buffered aqueous solution where the pH of the buffered aqueous peptide solution is set to that of optimal stability and solubility for the specific peptide. The peptide is then dried (for example, via freeze drying or spray drying) to a powder from the aqueous solution such that the ionization profile of the peptide molecule in the powder may be about equal to the ionization profile of the peptide molecule in the aqueous solution from which it was dried. When the peptide powder is then solubilized in an aprotic polar solvent system, the ionization profile of the peptide molecule may be about equal to the ionization profile of the peptide molecule in the powder. Accordingly, the ionization profile of the peptide molecule in the aprotic polar solvent system is about equal to the ionization profile of the peptide molecule in the buffered aqueous solution (see, e.g., U.S. Pat. Nos. 9,649,364, 10,485,850, and 11,020,403, the disclosures of which are incorporated by reference herein in their entireties).

The requirement for drying a therapeutic molecule from a buffered aqueous solution in order to optimize the ionization profile of the molecule and impart pH memory before it is solubilized in an aprotic polar solvent often imposes significant added costs, both in terms of time and expense, to the formulation development pathway. In particular, the drying process is well known to impose several stresses on the therapeutic molecule, and additional excipients (e.g., lyoprotectants such as trehalose and sucrose, and/or surfactants such as polysorbate 80) must be included in the aqueous solution in sufficient amounts to protect the therapeutic molecule, thereby increasing the cost and complexity of the formulation. Further, the drying process (e.g., spray drying, freeze drying) must often be optimized for a given therapeutic molecule, both at the lab-scale during initial research and development where the process is initially developed, and then during the manufacturing-scale as the process is scaled-up and transferred to instruments and facilities capable of producing commercial-scale batches. Consequently, the combination of initially developing and optimizing a drying process for a given therapeutic molecule, coupled with the time and costs associated with both transferring the method and incorporating an additional step in the manufacturing process can be very expensive. Without wishing to be bound by theory, it is believed that by providing a sufficient quantity of at least one ionization stabilizing excipient to achieve an appropriate or optimal ionization profile of the therapeutic molecule, electrostatic repulsion between therapeutic molecules possessing the same charge polarity (i.e., negatively or positively charged) may be sufficient in magnitude to prevent physical degradation (e.g., via short-range hydrophobic interaction between molecules that lead to aggregation). This is especially important for molecules that exhibit a tendency to aggregate in solution, particularly as the concentration of the molecule in solution is increased. Further, by controlling and optimizing the extent of the ionization (i.e., protonation or deprotonation) of the therapeutic agent, chemical degradation can be minimized, as, for example, an excess of protonation may promote chemical instability via degradative reactions such as oxidation (for example, oxidation of methionine residues) and fragmentation (for example, cleavage of the peptide backbone). Accordingly, for some therapeutic molecules there may be an optimal or beneficial ionization profile achieved via protonation or deprotonation such that physical and/or chemical degradation reactions are minimized. For a therapeutic small molecule or peptide, the extent of ionization (i.e., protonation or deprotonation)

required for stability, and thus the amount of the ionization stabilizing excipient required in the solution, will depend on, among other things, the structure of the therapeutic molecule and its concentration in the solution.

Each molecule that functions as an ionization stabilizing excipient will exhibit a certain tendency to donate protons to, or accept protons from, the therapeutic molecule(s) and/or additional drug substance/powder components (e.g., salts, counterions, buffer molecules, etc.) in a given solvent system; the tendency to donate protons may be referred to as the relative acidic strength of the molecule, while the tendency to accept protons may be referred to as the relative basic strength of the molecule. As a non-limiting example, for a fixed concentration of a proton-donating molecule, (and for simplicity it is assumed only monoprotic molecules in this example) molecules that have a greater acidic strength will protonate the therapeutic molecule to a greater extent than a weaker acid. Accordingly, the concentration of a given proton-donating molecule (ionization stabilizing excipient) required to achieve an appropriate or optimal ionization profile for the therapeutic molecules will be inversely proportional to its acidic strength. These and other non-limiting aspects of the present invention are discussed herein.

The formulation can comprise an ionization stabilizing excipient at a concentration of at least or about 0.01, 0.1, 0.5, 1, 10, 15, 20, 25, 30, 35, 40, 45, or 50 mM, and all ranges and concentrations therebetween, to at most or about 10, 15, 20, 25, 30, 50, 75, 100, 500, 1000 mM, and all ranges and concentrations therebetween, or up to the solubility limit of the ionization stabilizing excipient in the aprotic polar solvent system. The appropriate amount of ionization stabilizing excipient to be included can be readily determined based on the charge profile of the therapeutic agent that is being solubilized in the aprotic polar system. In particular, the amount of ionization stabilizing excipient to be added to the aprotic polar solvent optimally is enough to result in an ionization stabilizing excipient that is about 2×-3× mol acid per mol of the API in the final formulation (e.g., ~14 mM acid for a 5 mg/ml (~6.4 mM) solution of levothyroxine sodium; ~10 mM acid for a 5 mg/mL (~5 mM) solution of levothyroxine free acid), i.e., a molar concentration ratio of about 2:1 to about 3:1, and preferably about 2.5:1, ionization stabilizing excipient to API. In certain aspects, the ionization stabilizing excipient concentration is between about 0.1 mM to about 100 mM, particularly about 1 mM to about 35 mM, e.g., about 1 mM, about 2 mM, about 5 mM, about 10 mM, about 15 mM, about 20 mM, about 25 mM, about 30 mM and about 35 mM, and all ranges and concentrations therebetween. Certain preferred such aspects comprise the ionization stabilizing excipient at a concentration selected from the range of from about 20 mM to about 32 mM, including about 20 mM, about 21 mM, about 22 mM, about 23 mM, about 24 mM, about 25 mM, about 26 mM, about 27 mM, about 28 mM, about 29 mM, about 30 mM, about 31 mM and about 32 mM, and all ranges and concentrations therebetween. In certain such aspects, the formulations of the invention comprise the ionization stabilizing excipient at a concentration of about 26 mM to about 32 mM, particularly about 26 mM, about 27 mM and about 28 mM, about 29 mM, about 30 mM, about 31 mM and about 32 mM, and all ranges and concentrations therebetween. In certain embodiments, the ionization stabilizing excipient may be a suitable mineral acid, such as hydrochloric acid, sulfuric acid, nitric acid, phosphoric acid and the like. Particularly preferred mineral acids are hydrochloric acid and sulfuric acid. In certain aspects, the ionization stabilizing excipient may be an organic acid, such as an amino acid, amino acid derivative, or the salt of an amino acid or amino acid derivative (examples include glycine, trimethylglycine (betaine), glycine hydrochloride, and trimethylglycine (betaine) hydrochloride). In a further aspect, the amino acid can be glycine or the amino acid derivative trimethylglycine.

In certain aspects, the aprotic polar solvent can be deoxygenated prior to preparation of the formulation. Many different techniques can be used in the context of the present invention to deoxygenate or remove oxygen from aprotic polar solvents (degasification or deoxygenation). For instance, it is contemplated that deoxygenation can, but is not limited to, remove oxygen that is dissolved in a liquid aprotic polar solvent either by the liquid alone, by the liquid and other solute molecules (e.g., micelles, cyclodextrins, etc.), or by other solute molecules alone. Non-limiting examples of deoxygenation techniques include placing the aprotic polar solvent under reduced pressure and/or heating the liquid to decrease the solubility of dissolved gas, fractional distillation, membrane degasification, substitution by inert gas, using a reducing agent, freeze-pump-thaw cycling, or long time storage in a container with air-locks. In one embodiment, the aprotic polar solvent is deoxygenated by vacuum degasification. In another embodiment, the aprotic polar solvent is deoxygenated by using a deaerator. In one instance, the deaerator is a tray-type or cascade type deaerator. In another instance, the deaerator is a spray-type deaerator. In yet another embodiment, the aprotic polar solvent is deoxygenated using a gas-liquid separation membrane. In one instance, the aprotic polar solvent is degassed using a gas-liquid separation membrane and reduced pressure. In one embodiment, a non-oxygen gas (e.g., $N_2$) is bubbled through the liquid to replace or reduce oxygen in the aprotic polar solvent. In one instance, the gas bubbled through the aprotic polar solvent is argon, helium, nitrogen, an inert gas, and/or hydrogen gas, preferably nitrogen gas. In another instance, the gas is bubbled through the aprotic polar solvent using a gas-stripping column. In yet another embodiment, the aprotic polar solvent is deoxygenated by one or more reducing agent(s). Non-limiting examples of reducing agents include ammonium sulfite, hydrogen gas, active deoxygenating metals, copper, tin, cadmium, Wood's metal alloy (50% bismuth, 25% lead, 12.5% tin, and 12.5% cadmium), etc. In yet another embodiment, the aprotic polar solvent is degassed by freeze-pump-thaw cycling (e.g., at least 1, 2, 3, or more cycles can be used). In one instance, the freeze-pump-thaw cycle comprises freezing the aprotic polar solvent under liquid nitrogen, applying a vacuum, and then thawing the solvent in warm water. In one embodiment, the aprotic polar solvent is deoxygenated by long time storage in a steel, glass, or wood container. In another embodiment, the aprotic polar solvent is sonicated, ultrasonicated, or stirred during deoxygenation.

Once treated or deoxygenated, the aprotic polar solvents may have less than 0.1 mM of dissolved oxygen, preferably less than 0.05 mM of dissolved oxygen. Methods known to those of skill in the art can be used to determine the amount of dissolved oxygen in any given aprotic polar solvent (e.g., a dissolved oxygen meter or probe device can be used such as the Dissolved Oxygen Probe commercially available by Vernier (Beaverton, Oregon, USA)).

In certain aspects, the formulations disclosed in the present application can be prepared and/or sealed under an inert gas atmosphere. Common methods include backfilling the primary container-closure system (e.g., vials) to provide an inert gas (e.g., nitrogen, argon) headspace. A secondary container-closure system (e.g., sealed foil pouches) may also be sealed under an inert gas environment.

I. Formulations

Formulations of the present invention include a therapeutic agent present in an aprotic polar solvent system containing at least one ionization stabilizing excipient and optionally one or more additional pharmaceutically acceptable excipients. The therapeutic agent can be dissolved (e.g., fully or partially solubilized) or suspended (fully or partially) in the aprotic polar solvent system.

In some embodiments, the therapeutic agent is present in an aprotic polar solvent that further comprises one or more ionization stabilizing excipients, such as those described hereinabove and at the concentrations described hereinabove. In other embodiments, the therapeutic agent is present in an aprotic polar solvent that is "neat," i.e., that does not contain a co-solvent or, if it contains a co-solvent does not contain a co-solvent other than water. In other embodiments, the therapeutic agent is present in a solvent system that is a mixture of two or more aprotic polar solvents and a moisture or water content greater than 10% v/v (i.e., an aprotic polar solvent system). An example would be a solvent system comprising a 75/25 (% v/v) mixture of DMSO and NMP, with a total moisture content of greater than 10% (v/v). In some embodiments, however, a co-solvent can be used, where in one or more aprotic polar solvents are mixed with a co-solvent. Non-limiting examples of co-solvents include (explicitly excluding water) ethanol, propylene glycol (PG), glycerol, and mixtures thereof. The co-solvent may be present in the formulation in an amount ranging from about 0.1% (w/v) to about 50% (w/v), e.g., about 0.1%, about 0.5%, about 1%, about 5%, about 10%, about 15%, about 20%, about 25%, about 30%, about 35%, or about 40% (w/v). In some embodiments, the co-solvent is present in the formulation in an amount ranging from about 10% (w/v) to about 50% (w/v), from about 10% (w/v) to about 40% (w/v), from about 10% (w/v) to about 30% (w/v), from about 10% (w/v) to about 25% (w/v), from about 15% (w/v) to about 50% (w/v), from about 15% (w/v) to about 40% (w/v), from about 15% (w/v) to about 30% (w/v), or from about 15% (w/v) to about 25% (w/v).

Certain preferred but non-limiting exemplary formulations of the invention suitably used for treating or preventing hypothyroidism, or diseases or disorders associated therewith or arising therefrom, comprise levothyroxine at a concentration of about 5 mg/mL or 10 mg/mL, dissolved in a solution comprising DMSO and an ionization stabilizing ingredient such as sulfuric acid at a concentration of about 10 mM to about 15 mM, more particularly about 13 mM to about 15 mM for a 5 mg/mL levothyroxine formulation, and of about 25 mM to about 35 mM, e.g., about 26 mM to about 32 mM for a 10 mg/mL levothyroxine formulation, and all ranges and concentrations therebetween.

Still further, the formulations of the present invention can include one or more other excipients in addition to the at least one ionization stabilizing excipient. In some embodiments, the other excipient is selected from sugars, salts, starches, sugar alcohols, antioxidants, chelators, and preservatives. Examples of suitable sugars excipients include, but are not limited to, trehalose, glucose, sucrose, etc. Examples of suitable starches for stabilizing excipients include, but are not limited to, hydroxyethyl starch (HES). Examples of suitable sugar alcohols (also referred to as polyols) for stabilizing excipients include, but are not limited to, mannitol and sorbitol. Examples of suitable antioxidants include, but are not limited to, ascorbic acid, cysteine, methionine, monothioglycerol, sodium thiosulphate, sulfites, BHT, BHA, ascorbyl palmitate, propyl gallate, N-acetyl-L-cysteine (NAC), and Vitamin E. Examples of suitable chelators include, but are not limited to, EDTA, EDTA disodium salt (edetate disodium), tartaric acid and salts thereof, glycerin, and citric acid and salts thereof. Examples of suitable inorganic salts include, but are not limited to, sodium chloride, potassium chloride, calcium chloride, magnesium chloride, calcium sulfate, magnesium sulfate, zinc sulfate and zinc acetate. Examples of suitable preservatives include, but are not limited to, benzyl alcohols, methyl parabens, metacresol, propyl parabens, and mixtures thereof. Additional formulation components include local anesthetics, such as lidocaine or procaine. In some embodiments, the additional stabilizing excipient is present in the formulation in an amount ranging from about 0.01% (w/v) to about 60% (w/v), from about 1% (w/v) to about 50% (w/v), from about 1% (w/v) to about 40% (w/v), from about 1% (w/v) to about 30% (w/v), from about 1% (w/v) to about 20% (w/v), from about 5% (w/v) to about 60% (w/v), from about 5% (w/v) to about 50% (w/v), from about 5% (w/v) to about 40% (w/v), from about 5% (w/v) to about 30% (w/v), from about 5% (w/v) to about 20% (w/v), from about 10% (w/v) to about 60% (w/v), from about 10% (w/v) to about 50% (w/v), from about 10% (w/v) to about 40% (w/v), from about 10% (w/v) to about 30% (w/v), or from about 10% (w/v) to about 20% (w/v). In some embodiments, the additional stabilizing excipient is present in the formulation in an amount that is about, at most, or at least 0.01, 0.1, 0.5, 1, 2, 3, 4, 5, 6, 7, 8, 9, 10, 15, 20, 25, 30, 35, 40, 45, 50, 55, or 60% (w/v).

II. Therapeutic Agents

Therapeutic agents in the context of the present invention encompass peptide or protein compounds, small molecule drugs, and pharmaceutically acceptable analogs and/or salts thereof. One of skill in the art is aware of which therapeutic agent is suitable for treating certain diseases or conditions and would be capable of administering effective amounts of a therapeutic agent in a formulation as described herein for the treatment of a disease or condition.

Non-limiting examples of small molecule drugs (and salts thereof) that can be used in the context of the present invention include, but are not limited to, levothyroxine, epinephrine, benzodiazepines, catecholemines, "triptans," sumatriptan, novantrone, chemotherapy small molecules (e.g., mitoxantrone), corticosteroid small molecules (e.g., methylprednisolone, beclomethasone dipropionate), immunosuppressive small molecules (e.g., azathioprine, cladribine, cyclophosphamide monohydrate, methotrexate), antiinflammatory small molecules (e.g., salicylic acid, acetylsalicylic acid, lisofylline, diflunisal, choline magnesium trisalicylate, salicylate, benorylate, flufenamic acid, mefenamic acid, meclofenamic acid, triflumic acid, diclofenac, fenclofenac, alclofenac, fentiazac, ibuprofen, flurbiprofen, ketoprofen, naproxen, fenoprofen, fenbufen, suprofen, indoprofen, tiaprofenic acid, benoxaprofen, pirprofen, tolmetin, zomepirac, clopinac, indomethacin, sulindac, phenylbutazone, oxyphenbutazone, azapropazone, feprazone, piroxicam, isoxicam), small molecules used to treat neurological disorders (e.g., cimetidine, ranitidine, famotidine, nizatidine, tacrine, metrifonate, rivastigmine, selegilene, imipramine, fluoxetine, olanzapine, sertindole, risperidone, valproate semisodium, gabapentin, carbamazepine, topiramate, phenytoin), small molecules used to treat cancer (e.g., vincristine, vinblastine, paclitaxel, docetaxel, cisplatin, irinotecan, topotecan, gemcitabine, temozolomide, imatinib, bortezomib), statins (e.g., atorvastatin, amlodipine, rosuvastatin, sitagliptin, simvastatin, fluvastatin, pitavastatin, lovastatin, pravastatin, simvastatin), and other taxane derivatives, small molecules used to treat tuberculosis (e.g., rifampicin), small molecule anti-fungal agents (e.g., fluconazole), small molecule anti-anxiety agents and small molecule anti-convulsant agents (e.g., lorazepam), small molecule anti-cholinergic agents (e.g., atropine), small molecule β-agonist drugs (e.g., albuterol sulfate), small molecule mast cell stabilizers and small molecule agents used to treat allergies (e.g., cromolyn sodium), small molecule anesthetic agents and small molecule anti-arrhythmic agents (e.g., lidocaine), small molecule antibiotic agents (e.g., tobramycin, ciprofloxacin), small molecule anti-migraine agents (e.g., sumatriptan), and small molecule anti-histamine drugs (e.g., diphenhydramine). In preferred embodiments, the small molecule is levothyroxine. Additional suitable examples of such small molecule drugs (and salts thereof) that may be advantageously used in the compositions and methods of the present invention will be familiar to the ordinarily skilled artisan based on information that is provided herein and that is readily available in the art.

Non-limiting examples of peptides and proteins (and salts thereof) that can be used in the context of the present invention include, but are not limited to, glucagon, pramlintide, insulin, leuprolide, an luteinizing-hormone-releasing hormone (LHRH) agonist, adrenocorticotropic hormone (ACTH), leuprolide, hirudin, parathyroid hormone (PTH), amylin, angiotensin(1-7), botulinum toxin, hematide, an amyloid peptide, gastric inhibitory peptide, an antibody (which may be monoclonal or polyclonal) or a fragment thereof, an immunogenic peptide (e.g., a peptide or peptide complex derived from a virus, a bacterium, or any prokaryotic or eukaryotic organism or cell thereof), an insulin-like growth factor, growth hormone releasing factor, anti-microbial factor, glatiramer, glucagon-like peptide-1 (GLP-1), a GLP-1 agonist, exenatide, analogs thereof, an amylin analog (pramlintide), and mixtures thereof. In some preferred aspects, the therapeutic agent is glucagon, insulin and/or pramlintide. Additional suitable examples of such peptides, proteins, peptide complexes and derivatives thereof that may be advantageously used in the compositions and methods of the present invention will be familiar to the ordinarily skilled artisan based on information that is provided herein and that is readily available in the art.

Each of the aforementioned small molecule drugs, peptides and proteins is well-known and commercially available from a variety of manufacturers and sources. Further, the amount of the small molecule drugs, peptides and proteins in the dosage formulations provided by the present invention can be varied depending on currently acceptable amounts, subject/patient needs (e.g., age, health, weight, nature and extend of symptom), and the like; such amounts are readily determined by one of ordinary skill in the pharmaceutical and pharmacological arts based on information that is readily available.

The therapeutic agents provided by the manufacturer or commercial source are typically provided in a powdered form for dissolution into the formulations as described herein. A number of known techniques can be used to form a powdered agent for dissolution.

Any suitable dosage of small molecule drugs, peptides and proteins (each, an "active pharmaceutical ingredient" or "API") can be formulated in the stable formulations of the present invention. Generally, the API (or, in embodiments comprising two or more APIs, each of the APIs) is present in the formulation in an amount ranging from about 0.1 μg/mL up to the solubility limit of the API. In certain such embodiments, the dosage ranges from about 0.1 μg/mL to about 500 mg/mL, or up to about 1 mg/mL, about 2.5 mg/mL, about 5 mg/mL, about 7.5 mg/mL, about 10 mg/mL, about 15 mg/mL, about 20 mg/mL, about 25 mg/mL, about 50 mg/mL, about 75 mg/mL, about 100 mg/mL, about 150 mg/mL, about 200 mg/mL, about 250 mg/mL, about 300 mg/mL, about 350 mg/mL, about 400 mg/mL, about 450 mg/mL or about 500 mg/mL, and all dosages between the two ends of each range described herein. In some embodiments, the small molecule API is levothyroxine, which is present in the formulation in an amount ranging from about 2 mg/mL to about 40 mg/mL, advantageously about 5 mg/mL, about 10 mg/mL, about 15 mg/mL, about 20 mg/mL or about 40 mg/mL. In other embodiments, the levothyroxine is present in the formulation in an amount ranging from about 3 mg/mL to about 20 mg/mL, and preferentially 5 mg/mL or 10 mg/mL. For subcutaneous or intramuscular injection into humans in some embodiments of the invention, the formulations are preferentially introduced into the subject, e.g., a human or a veterinary animal, in a volume sufficient to deliver between about 500 μg to about 1500 μg of levothyroxine, and all amounts within that range. In certain such embodiments, the levothyroxine is injected into the subject in a volume suitable to deliver about 600 μg, about 1200 μg or about 1500 μg of levothyroxine per injection. Again, it will be readily apparent to those of skill that the dosage can be varied depending on the API used and the disease, disorder or condition to be treated, based on information provided herein and that is readily available in the relevant arts.

In some embodiments, the formulations of the present invention further comprise an antioxidant. In other embodiments, the formulations further comprise a chelator. In still other embodiments, the formulations of the present invention further comprise a preservative, sugar (e.g., a monosaccharide, a disaccharide or a polysaccharide, e.g., trehalose dihydrate), a sugar alcohol (e.g., mannitol, xylitol or erythritol), a polyol, a surfactant and/or a salt.

III. Therapeutic Methods

In another aspect, the present invention provides methods of treating or preventing diseases, conditions, or disorders by administering to a subject a therapeutic agent for treating or preventing a disease, condition, or disorder in a stable formulation as described herein in an amount effective to treat, alleviate, ameliorate or prevent the disease, condition, or disorder. The therapeutic agent of the invention can be administered intramuscularly, intracutaneously or subcutaneously, preferably subcutaneously or intradermally, and most preferably subcutaneously, in the prevention, diagnosis, alleviation, treatment, or cure of diseases or physical disorders in humans and veterinary animals.

In some embodiments, a therapeutic method of the present invention comprises treating hypothyroidism, or a disease or physical disorder arising from or associated with hypothyroidism, by administering to a subject having hypothyroidism or a disease or physical disorder associated therewith a therapeutic agent for hypothyroidism, preferably levothyroxine, in an amount effective to treat the hypothyroidism or the disease or physical disorder arising from or associated with hypothyroidism. The compositions and methods of the present invention are advantageously used in treating hypothyroidism regardless of its etiology, i.e., whether it arises from a primary cause or a secondary cause. Any condition that impacts the thyroid and causes it to create low levels of thyroid hormones is considered a primary cause of hypothyroidism, while a secondary cause is any condition, disorder or injury that causes the pituitary gland to fail resulting in its inability to secrete thyroid stimulating hormone (TSH) which signals the thyroid to secrete higher amounts of the thyroid hormones to overcome the imbalance that is a hallmark of hypothyroidism. Such diseases or disorders involving, associated with or attributed to hypothyroidism include, but are not limited to, thyroiditis, congenital hypothyroidism, autoimmune hypothyroidism (e.g., Hashimoto's Disease), ablation of the thyroid via surgical, radiological or chemical means (such as in treating hyperthyroidism or the effects thereof such as Grave's Disease or Thyroid Eye Disease), iodine deficiency, myxedema, myxedema coma/crisis, postpartum thyroiditis, certain viral illnesses, and the like. Patients afflicted with hypothyroidism report a number of symptoms, not all of which are associated with every case of hypothyroidism. Such symptoms include, for example, fatigue, peripheral neuropathy (especially experiencing numbness or tingling in the hands and/or fingers), weight gain, development of a goiter, fibromyalgia, body soreness including muscle weakness or joint pain, hypercholesterolemia, depression, hypothermia or increased sensitivity to cold temperatures, dryness/coarseness of skin and hair, hair loss, physical changes in the appearance of the face (e.g., drooping eyelids or puffiness in the eyes/face), cognitive or memory problems (often described as "brain fog"), and the like. By treating and/or preventing hypothyroidism, the levothyroxine-containing compositions and methods of the present invention lead to an improvement in or a restoration of the balance of thyroid hormones in the subject, and thus alleviation or reduction of the symptoms described above. In particular non-limiting exemplary embodiments, as described in the Examples below, the use of the formulations of the present invention, administered subcutaneously to the subject, can overcome the limitations of traditional daily oral (per os or "PO") administration of solid forms, e.g., tablets, of levothyroxine, by permitting a once-weekly, bimonthly or even monthly, administration of levothyroxine to the subject, thereby improving the patient experience and compliance with the treatment regimen devised and prescribed by the patient's medical practitioner or other healthcare provider.

In some embodiments, a therapeutic method of the present invention comprises treating hypoglycemia by administering to a subject having hypoglycemia a therapeutic agent for hypoglycemia in a storage stable formulation as described herein in an amount effective to treat the hypoglycemia. In some embodiments, the subject is administered a storage stable formulation comprising glucagon, in a manner that results in the release of glucagon from the site of administration into the bloodstream or tissues of the animal over a prolonged period of time (i.e., "sustained release"; see, e.g., U.S. Patent Publ. No. US 2021/0401945 A1, which is incorporated by reference herein in its entirety)) when compared to an immediate release formulation comprising glucagon. In such aspects, the disease, condition, or disorder to be treated with a stable formulation of the present invention is a diabetic condition. Examples of diabetic conditions include, but are not limited to, type 1 diabetes, type 2 diabetes, gestational diabetes, pre-diabetes, hyperglycemia, hypoglycemia, and metabolic syndrome. In some embodiments, the disease, condition, or disorder is hypoglycemia, including but not limited to diabetes-related hypoglycemia, exercise-induced hypoglycemia, and post-bariatric surgery hypoglycemia, or other types of hypoglycemia described herein and known to those of ordinary skill in the art (see, e.g., U.S. Pat. Nos. 9,649,364, 10,485,850, and 11,020,403, the disclosures of which are incorporated herein by reference in their entireties). In some embodiments, the disease, condition, or disorder is diabetes.

In some embodiments, a therapeutic method of the present invention comprises treating diabetes by administering to a subject having diabetes a therapeutic agent in a stable formulation as described herein in an amount effective to treat the diabetes. In some embodiments, the subject is administered a stable formulation comprising insulin. In some embodiments, the subject is administered a stable formulation comprising pramlintide. In some embodiments, the subject is administered a stable formulation comprising insulin and pramlintide. In some embodiments, the subject is administered a stable formulation comprising exenatide. In some embodiments, the subject is administered a stable formulation comprising glucagon and exenatide.

In certain aspects, formulations of the present invention comprising epinephrine can be administered to a subject at risk of or suspected of anaphylaxis. Epinephrine is indicated as an emergency treatment of Type I allergic reactions which can arise from multiple sources, including, but not limited to, foods, drugs and/or other allergens, allergen immunotherapy, diagnostic testing substances, insect stings and bites, and idiopathic or exercise-induced anaphylaxis.

Administered dosages for the small molecule drugs or peptide drugs as described herein for treating a disease, condition, or disorder (e.g., hypothyroidism, a diabetic condition, hypoglycemia, or anaphylaxis) are in accordance with dosages and scheduling regimens practiced by those of skill in the art, and as described herein. General guidance for appropriate dosages of all pharmacological agents used in the present methods is provided in Goodman and Gilman's The Pharmacological Basis of Therapeutics, 11th Edition, 2006, supra, and in the Physicians' Desk Reference (PDR), for example, in the 65th (2011) or 66th (2012) Eds., PDR Network, LLC, each of which is hereby incorporated herein by reference. The appropriate dosage of a small molecule drug or peptide drug for treating a disease, condition, or disorder as described herein will vary according to several factors, including the formulation of the composition, patient response, the severity of the condition, the subject's weight, and the judgment of the prescribing physician. Effective doses of the described formulations deliver a medically effective amount of a small molecule or peptide drug. The dosage can be titrated (i.e., increased or decreased over time), as required by an individual patient or as determined by medical personnel. Determination of an effective amount or dose of a small molecule drug or a peptide drug, and thus the appropriate amount or volume of the therapeutic formulations of the invention to be administered to the subject, therefore is well within the capability of those skilled in the art, especially in light of the detailed disclosure provided herein.

The formulations of the present invention may be used for parenteral administration, including, but not limited to, subcutaneous, intradermal, intramuscular, intranasal, buccal, transdermal or intravenous administration (e.g., by injection or by infusion). In some embodiments, the formulation is administered subcutaneously. The formulations can also be delivered transdermally, such as by topically applying the composition to skin (e.g., spreading the composition on skin or loading the composition onto a dermal patch and attaching the dermal patch to the skin).

The formulations of the present disclosure can be administered by infusion or by injection using any suitable device. For example, a formulation of the present invention may be placed into a syringe (e.g., a pre-filled syringe), a pen injection device, an auto-injector device, or a pump device. In some embodiments, the injection device is a multi-dose injector pump device or a multi-dose auto-injector device.

The formulation is presented in the device in such a fashion that the formulation is readily able to flow out of the needle upon actuation of an injection device, such as an auto-injector, in order to deliver the peptide drugs. Suitable pen/auto injector devices include, but are not limited to, those pen/auto injection devices manufactured by Becton-Dickinson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like.

In some embodiments, the formulations of the present invention are provided ready for administration in a vial, a cartridge, or a pre-filled syringe.

In additional embodiments, the formulations provided by the present invention may be used in certain diagnostic procedures. In particular such embodiments, a glucagon-containing formulation of the present invention can be administered to a mammal, such as a human or a veterinary animal, prior to, as an adjunct to, as a part of, or in conjunction with, one or more diagnostic procedures, thereby providing a method of diagnosing the disease or disorder in a patient suffering from or predisposed to the disease or disorder. Non-limiting examples of such diagnostic procedures in which a glucagon-containing formulation of the present invention may be suitably used include methods for diagnosing Alzheimer's Disease (see U.S. Pat. No. 4,727,041, incorporated herein by reference in its entirety) and growth hormone deficiency (see U.S. Pat. No. 5,065,747; see also Boguszewski, C. L., Endocrine 57:361-363 (2017), and Yuen, K. C. J., ISRN Endocrinology, vol. 211, Article ID 608056, pp. 1-6 (2011), doi: 10.5402/2011/608056; the disclosures of all of which are incorporated by reference herein in their entireties). Additional examples of such uses include in certain radiologic diagnostic procedures, particularly those used in diagnosing gastroenterologic conditions (non-limiting examples of which include abdominal obstructions, appendicitis, Barrett's esophagus, celiac disease, cancers, cirrhosis, Crohn's disease, diverticulitis, diverticulosis, ulcers, gallstones, gastric prolapse, gastritis, gastroesophageal reflux disease, hepatitis (A/B/C), hiatus hernia, inflammatory bowel disorder, hernia, irritable bowel syndrome, pancreatitis, perianal fissure, ulcerative colitis, and the like), during radiologic examinations of the gastrointestinal system to temporarily inhibit movement of the organs and connective tissues of the gastrointestinal tract in adult patients (see, e.g., product label for glucagon, lyophilized (NDC Code 63323-185-03), accessible at: https://dailymed.nlm.nih.gov/dailymed/drugInfo.cfm?setid=8c8acad6-44cc-43aa-966b-027e053be8f5; see also, Glucagon in Gastroenterology, J. Picazo, ed., Lancaster, England: MTP Press Ltd. (1979), especially Chapters 3-7, pp. 39-120; the disclosure of which is incorporated herein by reference). In such diagnostic methods, the glucagon-containing formulation of the invention is administered to the patient suffering from or predisposed to the disorder by any suitable method of introduction of such formulation into the body of the patient such as those described herein, e.g., intravenously at dosages of about 0.2 mg to about 0.75 mg about 1-10 minutes prior to the diagnostic test (e.g., the radiologic procedure), or intramuscularly or intradermally at dosages of about 1 mg to about 2 mg about 5-15 minutes prior to the diagnostic test (e.g., the radiologic procedure). Other suitable therapeutic and diagnostic methods of use of the formulations of the present invention will be readily familiar to the ordinarily skilled clinician or pharmacist based on the disclosure contained herein in view of information that is available in the art.

IV. Kits/Containers

Kits are also contemplated as being provided by certain aspects of the present invention. For instance, a formulation of the present invention can be included within a kit, which can include a container. In one aspect, for instance, the formulation can be comprised within a container that is ready to administer to a subject or be incorporated into a device configured to administer to a subject, without having to reconstitute or dilute the formulation. That is, the formulation to be administered can be stored in the container and be readily used as needed. In some embodiments, the container can be a device. The device can be a syringe (e.g., pre-filled syringe), a pen injection device, an auto-injector device, a device that can pump or administer the formulation (e.g., automatic or non-automatic external pumps (e.g., patch pumps, or pumps requiring an external infusion set), implantable pumps, etc.) or a perfusion bag. Suitable pen/auto-injector devices include, but are not limited to, those pen/auto-injection devices manufactured by Becton-Dickinson, Swedish Healthcare Limited (SHL Group), YpsoMed Ag, and the like. Suitable pump devices include, but are not limited to, those pump devices manufactured by Tandem Diabetes Care, Inc., Delsys Pharmaceuticals and the like. Suitable infusion sets include, but are not limited to, those manufactured/distributed/sold by Tandem Diabetes Care, Inc., Medtronic, Disetronic, YpsoMed Ag, Unomedical A/S and the like. Kits of the invention also can comprise one or more additional components, including but not limited to instructions for use of the kit and/or its components, one or more additional containers or compartments for holding the components of the kit, multiple containers or devices comprising the formulations of the invention, and the like.

EXAMPLES

Some embodiments of the present disclosure will be described in greater detail by way of specific examples. The following examples are offered for illustrative purposes and are not intended to limit any present invention in any manner. For example, those of skill in the art will readily recognize a variety of noncritical parameters, which can be changed or modified, without undue experimentation, to yield essentially the same results.

Example 1: Preparation of Stable Liquid Levothyroxine-Containing Formulations As has been noted elsewhere herein, liquid levothyroxine formulations have proven difficult to prepare in a standard aqueous environment, due to the general insolubility (≤0.1 mg/mL) of levothyroxine in water. For the treatment of hypothyroidism, daily doses exceeding 0.1 mg are typically required, which would necessitate a painful >1 mL injection volume. There is an aqueous-based commercial formulation (having organic cosolvents) that is marketed at multiple concentrations ranging from 20-100 µg/mL (e.g., 0.02-0.1 mg/mL), but these are intended only for intravenous administration to patients in a hospital setting and only indicated for the treatment of myxedema coma/crisis. At present there is no injectable formulation for the most commercially relevant use of levothyroxine (chronic hypothyroidism), which is currently treated with daily dosing of oral levothyroxine tablets. However, as described hereinabove, there can be considerable limitations with gastrointestinal absorption of levothyroxine, and patient compliance with a daily dosage regimen often is suboptimal.

The present inventors therefore attempted to solve the problem of low solubility of levothyroxine by employing a DMSO-based solvent system to achieve levothyroxine concentrations of at least 5-10 mg/mL (i.e., 10-20× greater than can be achieved with currently available aqueous-based formulations). These initial formulation studies were based on the discoveries of several of the present inventors that aprotic polar solvents such as dimethyl sulfoxide (DMSO) can be advantageously used to prepare liquid injectable solutions of other poorly water-soluble active pharmaceutical ingredients that also have poor stability in a standard aqueous environment, such as glucagon (see, e.g., U.S. Pat. Nos. 9,649,264, 10,485,850, and 11,020,403, the disclosures of which are incorporated herein in their entireties).

An initial study of the solubility of levothyroxine sodium in DMSO observed the API is soluble to at least 30 mg/mL, greatly improving the solubility of levothyroxine sodium relative to water. However, direct dissolution of levothyroxine sodium in DMSO (with no added excipients) caused rapid visual discoloration and chemical degradation (where the extent of discoloration generally correlates with degradation). In addition, following 9-10 days of storage at 45° C., 5 mg/mL levothyroxine (sodium salt) was almost completely degraded. Additionally, the chemical degradation appeared to be associated with the discoloration of the solution that was observed.

To attempt to overcome these discoloration and degradation problems, levothyroxine solutions were prepared with either the free acid or the sodium salt of levothyroxine dissolved in acidified DMSO, at a levothyroxine sodium concentration of 5 mg/mL. To prepare acidified DMSO solvents, DMSO was acidified with 0-10 mM $H_2SO_4$ (from a 1.0 N $H_2SO_4$ stock solution), and samples were stored in 2 mL glass vials (0.5 mL fill volume per vial) and stored at 45° C. upright for 9 days for an accelerated stability analysis without any secondary packaging (e.g., foil pouch). Samples were then photographed (to examine discoloration) and examined via reverse phase HPLC (to examine levothyroxine chemical stability), comparing day 0 samples to day 9 samples (vs. a sample of each formulation that was frozen and held at −20° C. as a "time 0" control).

Figure 1B:
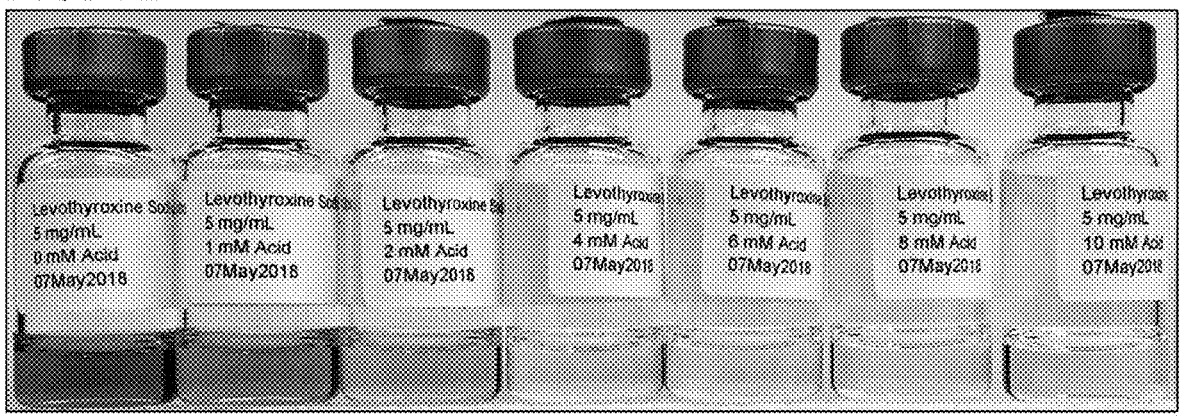
Figure 2A:
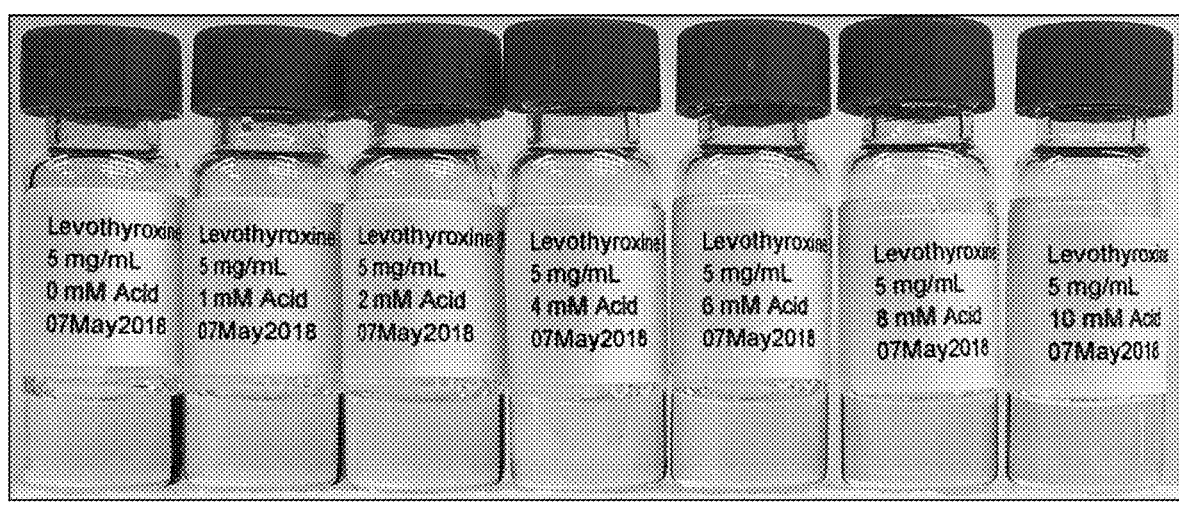
FIGS. 2A-2B are a series of photographs, showing the color of 5 mg/mL levothyroxine (free acid) formulations in DMSO with various concentrations of acid ($H_2SO_4$), shortly after preparation (FIG. 2A) or stored at 45° C. for 9 days (FIG. 2B).
Figure 2B:
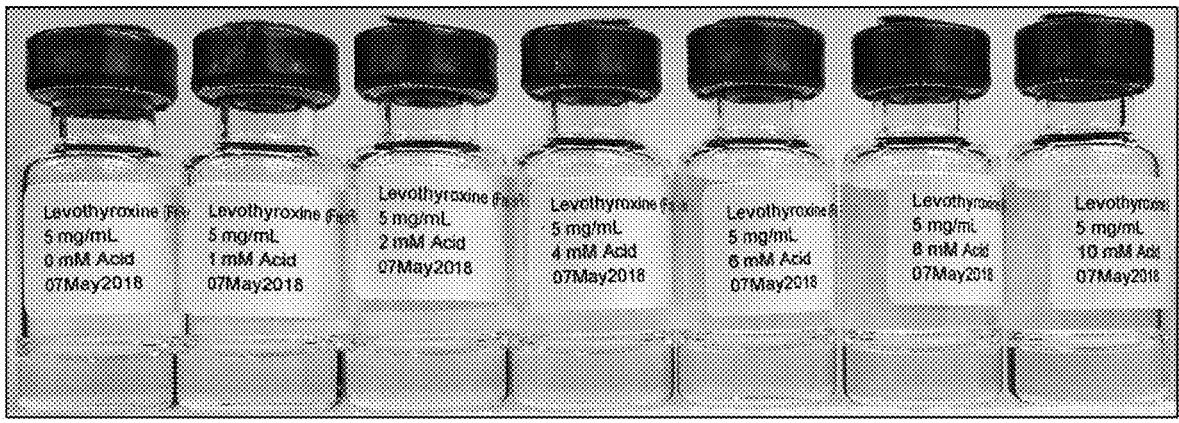

FIGS. 1 and 2 demonstrate the influence of acidified DMSO on the discoloration of 5 mg/mL levothyroxine after 9 days of storage at 45° C. FIG. 1 shows solutions of the sodium salt of levothyroxine on day 0 (i.e., shortly after the solutions were prepared) and following 9 days of storage (FIGS. 1A and 1B, respectively), while FIG. 2 shows solutions of levothyroxine free acid on day 0 and after 9 days of storage (FIGS. 2A and 2B, respectively), in varying concentrations of $H_2SO_4$ as indicated on the labels on each vial. As can be seen from these figures, the levothyroxine sodium salt demonstrated degradation-associated discoloration fairly quickly at concentrations of acid below 4 mM (FIG. 1A), and even more marked discoloration after 9 days of accelerated stability storage (FIG. 1B). Only the formulation comprising 10 mM acid demonstrated no significant discoloration. Similar results were observed for the levothyroxine free acid (FIG. 2), although these formulations did not show significant discoloration at day 0 (FIG. 2A) and a lower amount of discoloration at all concentrations of acid after 9 days of storage (FIG. 2B) compared to what was observed for the levothyroxine sodium salt (FIG. 1B).

Figure 3A:
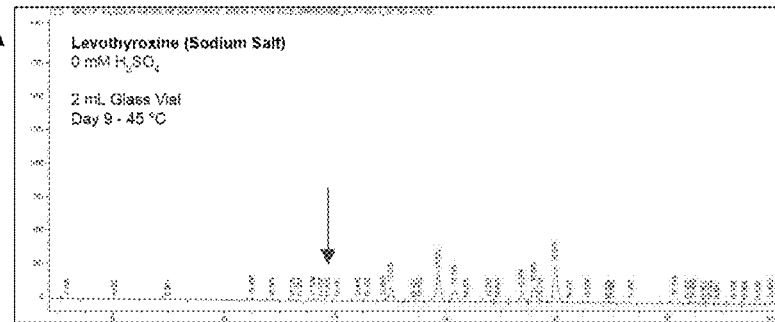
FIGS. 3A-3E are a series of reverse-phase HPLC (RP-HPLC) chromatograms of some of the levothyroxine (sodium salt) formulations depicted in FIG. 1, at various concentrations of acid ($H_2SO_4$) after storage for 9 days at 45° C. Red arrows in each chromatogram depict the intact levothyroxine peak; other peaks represent degradation products.
Figure 3B:
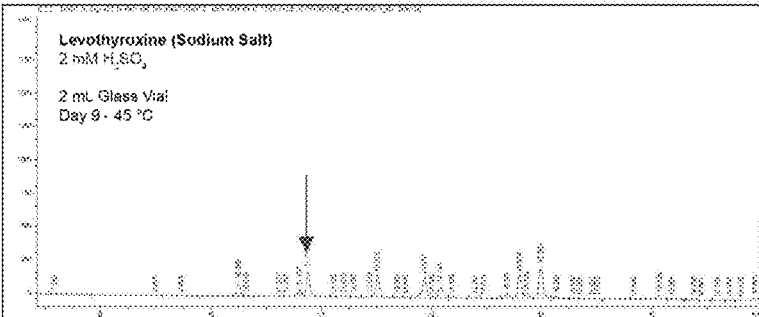
Figure 3C:
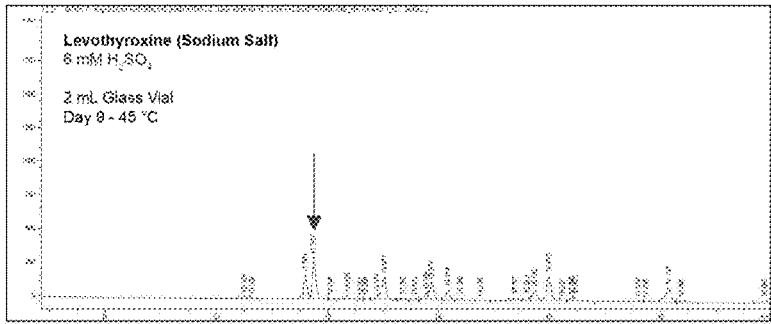
Figure 3D:
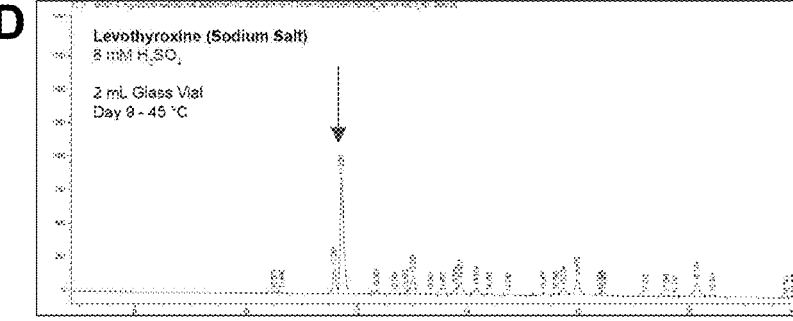
Figure 3E:
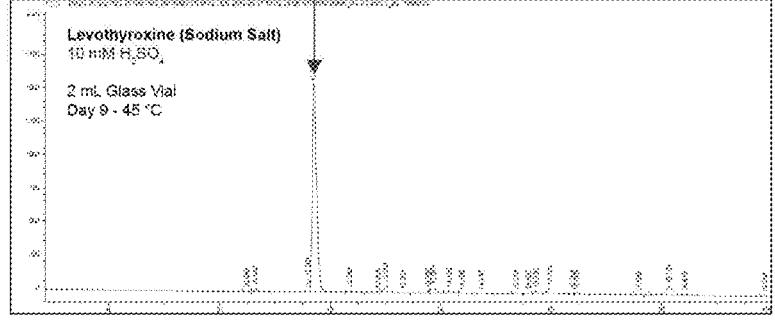
Figure 4A:
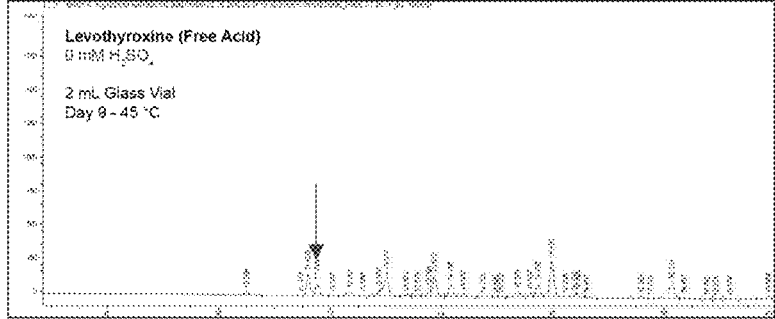
FIGS. 4A-4E are a series of reverse-phase HPLC (RP-HPLC) chromatograms of some of the levothyroxine (sodium salt) formulations depicted in FIG. 2, at various concentrations of acid ($H_2SO_4$) after storage for 9 days at 45° C. Red arrows in each chromatogram depict the intact levothyroxine peak; other peaks represent degradation products.
Figure 4B:
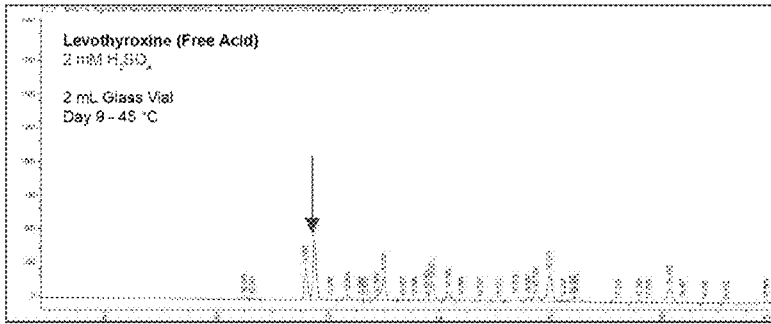
Figure 4C:
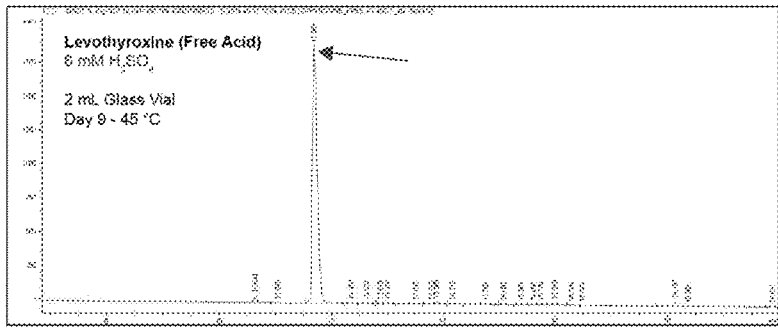
Figure 4D:
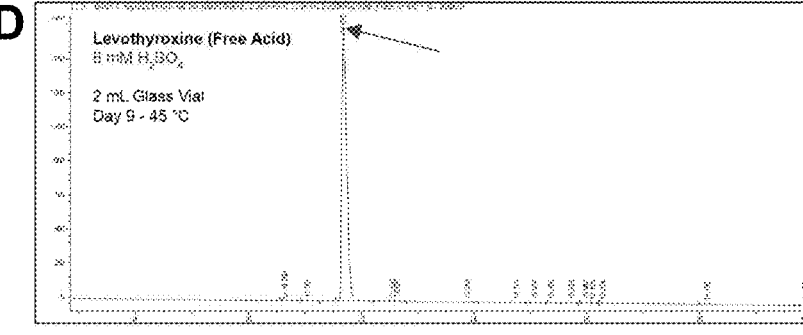
Figure 4E:
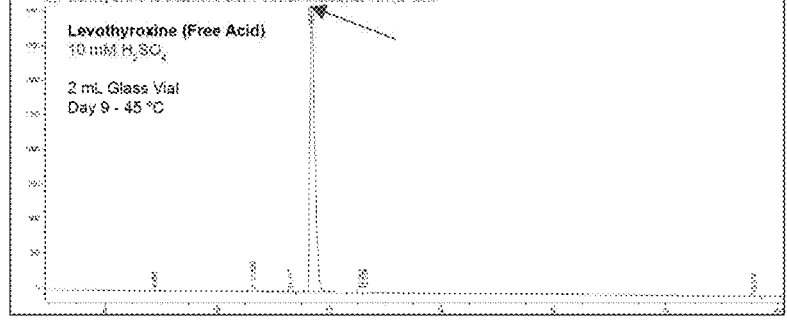

To determine if the discoloration observed with these formulations correlated with levothyroxine chemical degradation, samples of each vial were assessed via reverse phase HPLC (RP-HPLC). Samples were run on a Waters Symmetry300 C18 column (3.5 μm, 2.1 mm×100 mm, 300 Å) using a mobile phase gradient of 0.1% TFA in water (92% at time 0, 8% at 2 min, 92% at 30 min, 8% at 35 min, 8% at 43 min) and acetonitrile (8% at time 0, 92% at 2 min, 8% at 30 min, 92% at 35 min, 92% at 43 min), with a flow rate of 0.5 mL/min, a column temperature of 25° C. and the detector wavelength set at 223 nm. FIGS. 3 and 4 show the corresponding RP-HPLC chromatograms of some of the formulations shown in FIGS. 1 and 2, demonstrating the degradation of levothyroxine at low concentrations of acid in the formulation and improved stability at higher concentrations of acid, after 9 days of storage at 45° C. FIG. 3 shows chromatograms of solutions of the sodium salt of levothyroxine, while FIG. 4 shows chromatograms of solutions of levothyroxine free acid, both in DMSO including 0 mM $H_2SO_4$ (FIGS. 3A and 4A), 2 mM $H_2SO_4$ (FIGS. 3B and 4B), 6 mM $H_2SO_4$ (FIGS. 3C and 4C), 8 mM $H_2SO_4$ (FIGS. 3D and 4D), and 10 mM $H_2SO_4$ (FIGS. 3E and 4E). Red arrows in each figure show the intact levothyroxine peak. As can be observed from these figures, at low concentrations of acid (0-2 mM), extensive degradation is observed, with increasing acid content promoting chemical stability.

Taken together, the study results indicate that levothyroxine sodium (the standard API form of levothyroxine) is unstable when dissolved directly in DMSO. There is an almost immediate discoloration (light yellow-to-yellow) which gets over time (i.e., during storage stability studies), and the levothyroxine rapidly and extensively degrades and is virtually undetectable by 9 days at 45° C. Although the degradation of the free acid form of levothyroxine was not as extensive as that observed for the sodium salt, it still exhibited significant degradation at low concentrations of acid. Higher concentrations of acid (particularly $H_2SO_4$) were shown to promote chemical stability of both forms of levothyroxine, however. In particular, for the sodium salt, a sulfuric acid concentration of about 2× mol acid per mol of drug (i.e., ~14 mM acid for a 5 mg/mL (~6.4 mM) solution of levothyroxine sodium; ~10 mM acid for a 5 mg/mL solution of levothyroxine free acid) was necessary to significantly enhance the chemical stability of the drug under accelerated stability testing conditions. These results indicate that while levothyroxine is readily soluble in DMSO, the DMSO must be acidified first in order to ensure storage stability of the ensuing formulations.

Based on the results shown above, formulations of levothyroxine sodium were prepared at an acid concentration that promoted chemical stability and a moisture content of at least 4% (w/w). An exemplary such formulation was prepared having the following composition: 10 mg/mL levothyroxine sodium; 5.53% (w/v) trehalose dihydrate; 2.9% (w/v) mannitol; 26-28 mM sulfuric acid (from a 1.0 N stock solution) and DMSO. When these solutions were prepared, it was found that the formulation did not freeze when stored at refrigerated conditions (2-8° C.) and accelerated and real-time stability testing completed through the date of filing of this application has shown that the formulation is on track to achieve at least 2 years of refrigerated storage stability (using a 95% API content stability specification). The overall moisture content of the formulation was ~5% when prepared using 1.0 N $H_2SO_4$. The moisture content of this formulation was due almost entirely to the added sulfuric acid (with a minor contribution from the trehalose dihydrate), which at 26 mM (from a 1.0 N (0.5 M) stock solution) results in a moisture content~5% (w/w). When prepared using concentrated acid (e.g., 10 N), the overall moisture content of the formulation could be reduced to about ~1% without any significant impact on storage stability.

Figure 5:
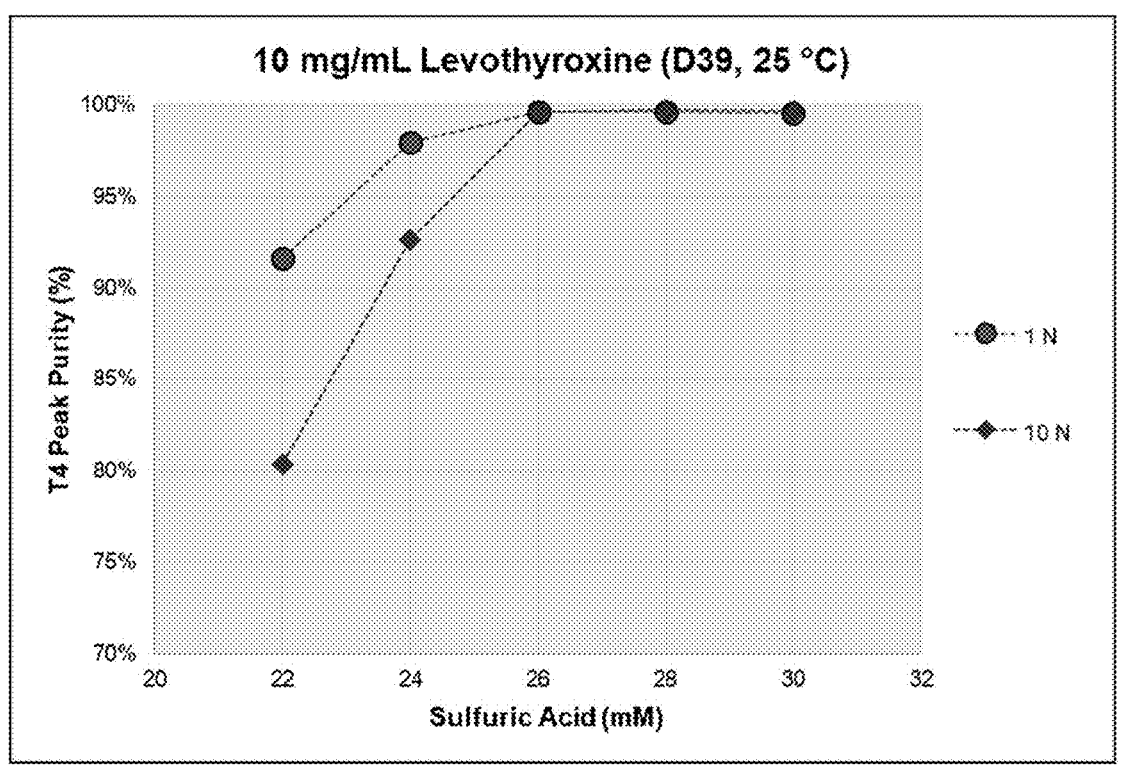
FIG. 5 is a line graph showing the effect of acid concentration on levothyroxine (T4) stability in DMSO formulations, as measured by percent T4 peak purity.

It is important to note that 10 mg/mL levothyroxine sodium corresponds to a molar concentration of approximately 13 mM. Using the 2-to-1 molar ratio of acid-to-drug described above in this Example, a sulfuric acid concentration of at least approximately 26 mM is required to promote stability. An example of how acid concentration influence stability of a 10 mg/mL is provided in FIG. 5 (note that T4 is an alternative, commonly used shorthand name for levothyroxine). As seen in this figure, when insufficient acid is added (<26 mM) extensive chemical degradation (and minor discoloration is observed), consistent with the photographic and chromatographic results shown in FIGS. 1-4 above. Above the approximate 26 mM acid threshold, however, chemical stability essentially plateaus.

An example of the stability that can be achieved using this formulation approach at multiple temperatures for up to 6 months is shown in Table 1, which represents the purity of T4 (levothyroxine sodium) in the 10 mg/mL, 26-28 mM acid DMSO formulations described above, over time at various storage temperatures. Results shown are measurements of T4 vs. T3 (triiodothyronine, the main degradation product of T4), determined as described above via RP-HPLC. In this table, the higher the percentage of T4 and the lower the percentage of T3, the less degradation observed in the levothyroxine formulations over time.

TABLE 1

| | | | 25° C./ | 30° C./ |
|---|---|---|---|---|
| Days | −20° C. | 2-8° C. | 60% RH | 65% RH |
| | | T4 | | |
| 40 | 100.0% | 100.0% | 99.6% | 99.2% |
| 70 | 99.6% | 99.5% | 98.8% | 97.7% |
| 92 | 99.5% | 99.5% | 98.5% | 96.8% |
| 184 | 99.9% | 99.6% | 97.5% | 94.4% |
| | | T3 | | |
| 40 | 0.0% | 0.0% | 0.3% | 0.70% |
| 70 | 0.0% | 0.0% | 0.6% | 1.3% |
| 92 | 0.0% | 0.0% | 0.8% | 1.7% |
| 184 | 0.0% | 0.1% | 1.7% | 3.6% |

Stability of Levothyroxine Formulations

Taken together, these results demonstrate that an exemplary levothyroxine formulation of the present invention comprising 10 mg/mL levothyroxine in a DMSO solution that has been acidified with 26-28 mM $H_2SO_4$, and an exemplary levothyroxine formulation of the invention comprising 5 mg/mL levothyroxine sodium in a DMSO solution that has been acidified with 13-15 mM $H_2SO_4$, are stable, even at room temperature, for at least 6 months. More recent data (not shown) have demonstrated that these levothyroxine formulations are storage stable for at least two years under refrigerated conditions (4° C.-10° C.). At these concentrations, these formulations of the present invention represent the first liquid, ready-to-use formulations of levothyroxine that can be administered weekly for the treatment of chronic hypothyroidism, which is the primary use of levothyroxine, thereby providing distinct advantages in terms of patient convenience and compliance over the oral levothyroxine formulations that are typically used in treating chronic hypothyroidism.

Example 2: Pre-Clinical Studies Using Liquid Levothyroxine-Containing Formulations Considering the formulation stability results described in Example 1, it was of interest to examine the pharmacokinetics of such exemplary levothyroxine formulations of the invention in pre-clinical studies using laboratory animals.

These studies were conducted in Göttingen minipigs (4- to 6-month-old males) obtained from Marshall Bioresources (Syracuse, NY). Nine levothyroxine formulations were prepared, all comprising 10 mg/mL levothyroxine in acidified DMSO using the XeriSol™ formulation platform (Xeris Pharmaceuticals, Inc.; Chicago, IL) as described above in Example 1, and as has been previously described for other active pharmaceutical ingredients (see, e.g., U.S. Pat. Nos. 9,649,364, 10,485,850, and 11,020,403, the disclosures of which are incorporated by reference herein in their entireties). To also study the impact on the pharmacokinetics of including sustained release excipients in the formulations, several of the formulations also received certain concentrations of PLGA at various molecular weights and concentrations. The formulations prepared are listed below in Table 2.

TABLE 2

Test Formulations

| Treatment Group No. | Formulation |
|---|---|
| XS-1 (XP-8121) | Xerisol ™ 10 mg/mL levothyroxine formulation: 10 mg/mL levothyroxine sodium; 5.53% (w/v) trehalose dihydrate; 2.9% (w/v) mannitol; 26-28 mM sulfuric acid (from a 1.0N stock solution) and DMSO |
| XS-2 | XS-1 + 20% PLGA-low molecular weight-acid terminated |
| XS-3 | XS-1 + 30% PLGA-low molecular weight-acid terminated |
| XS-4 | XS-1 + 30% PLGA-mid molecular weight-ester terminated |
| XS-5 | XS-1 + 30% PLGA-low molecular weight-ester terminated |
| XS-6 | XS-1 + 30% PLGA-high molecular weight-ester terminated |
| XS-7 | XS-1 + 30% PLGA-very high molecular weight-ester terminated |
| XS-8 | XS-1 + 40% PLGA-mid molecular weight-ester terminated |
| XS-9 | XS-1 + 40% PLGA-high molecular weight-ester terminated |

Göttingen minipigs (n=12) were randomized based on body weights into treatment groups 1, 2 and 3 as per Table 2. Three groups of four minipigs per group received a single dose of one of the levothyroxine formulations described in Table 2. Wash out period was a minimum of 21 days following which the animals were re-dosed with the next set of formulations. Animals were transferred to a subsequent group following washout of each dose, as follows: Group 1→Group 4→Group 7; Group 2→Group 5→Group 8; Group 3→Group 6→Group 9. All formulations were administered subcutaneously at a fixed dose of 10 mg per animal. Blood samples were taken at the following time points for measurement of plasma levothyroxine concentration: pre-dose (baseline), and 0.083, 0.25, 0.5, 1, 2, 4, 6, 8, 24, 48, 72, 96, 120, 144, 192, 240, 288, 366 hours post-dose.

A bioanalytical method to determine levothyroxine (L-thyroxine) concentrations in minipig plasma was developed by Pyxant Labs Inc. The method was qualified over the range of 2.00 to 4000 ng/mL. This method utilizes a surrogate matrix approach for the quantitation of L-thyroxine, in which 5% bovine serum albumin (BSA) in water is used because L-thyroxine is endogenous. Samples were prepared by a protein precipitation extraction procedure. Extracts were analyzed by liquid chromatography/tandem mass spectrometry (LC-MS/MS) in positive ionization mode under optimized conditions for detection of levothyroxine and thyroxine-$^{13}$C6 (internal standard) positive ions formed by electrospray ionization.

Noncompartmental pharmacokinetic analysis was conducted on baseline-adjusted levothyroxine levels for each animal using Phoenix 64 software version 8.2.0.4383 (Certara, Inc.; Princeton, NJ). Pharmacokinetic parameters derived included Cmax, Tmax, AUClast, AUC144-336 and AUC∞. Values for λz and t½ were not determined due to high fluctuations of plasma levels in the terminal phase. Results of each of these analyses are presented in FIGS. 6-12.

Figure 6A:
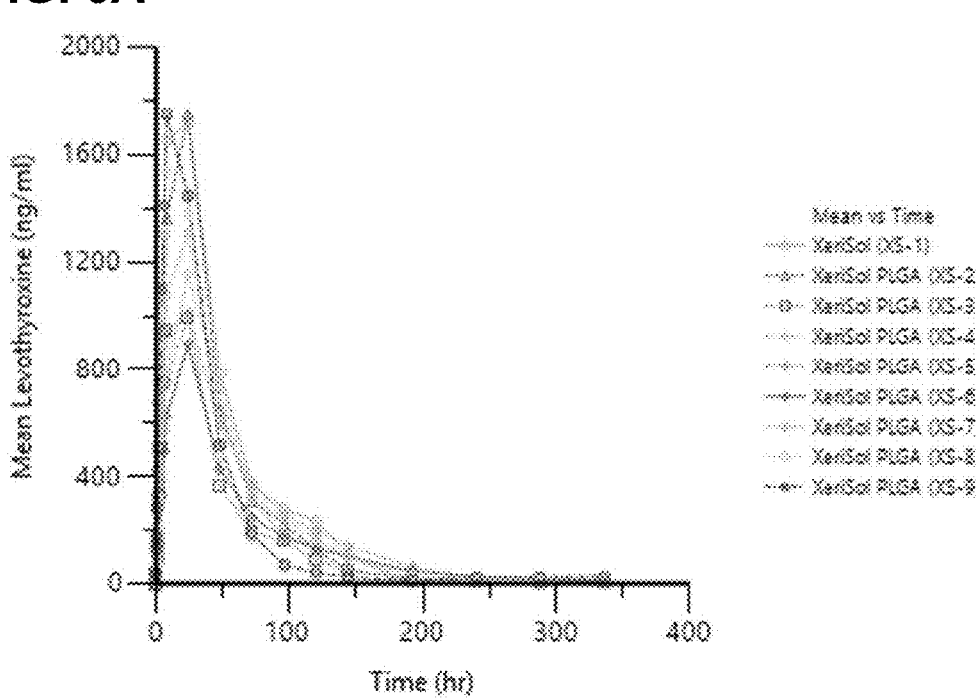
FIGS. 6A-6B are a pair of line graphs showing mean plasma levothyroxine concentration in minipigs dosed with various formulations of the present invention, plotted on a linear scale (FIG. 6A) or a logarithmic scale (FIG. 6B).
Figure 6B:
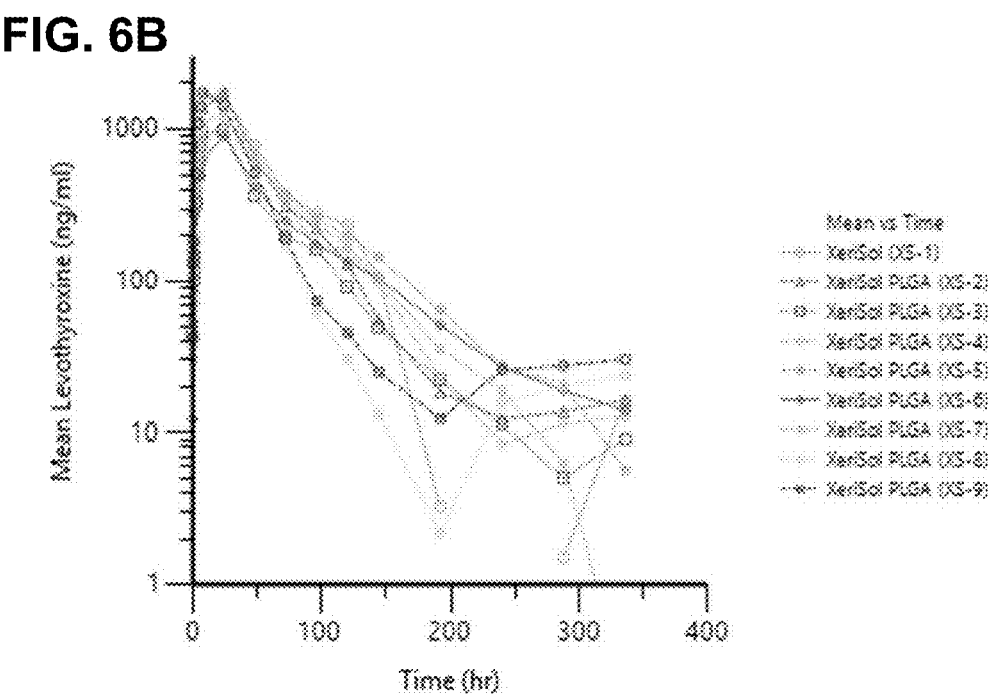
Figure 7:
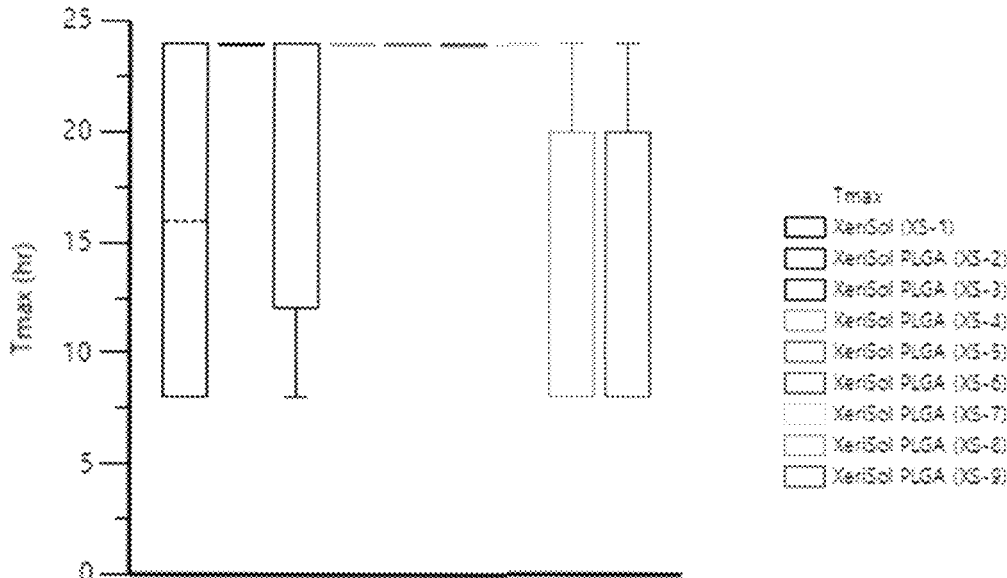
FIG. 7 is a box plot showing mean Tmax (in hours) for levothyroxine formulations of the present invention administered subcutaneously to minipigs.
Figure 8:
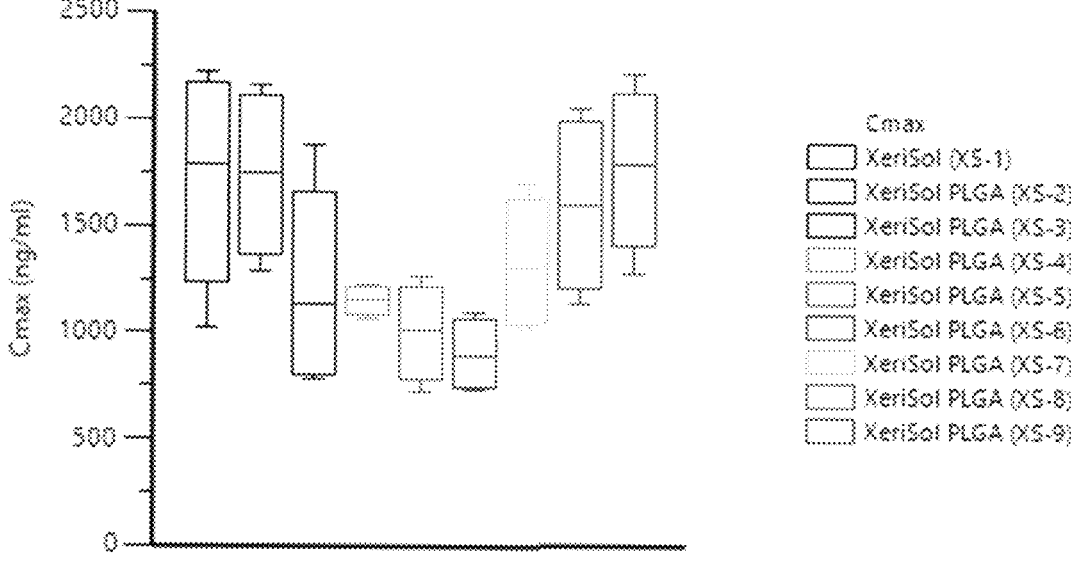
FIG. 8 is a box plot showing mean Cmax (ng/mL) for levothyroxine formulations of the present invention administered subcutaneously to minipigs.

All animals demonstrated quantifiable increase in baseline adjusted plasma levothyroxine concentrations after SC administration of test articles (FIG. 6). XeriSol™ levothyroxine (XS-1) plasma concentration—time curves were characterized by a gradual absorption reaching Cmax at a median post-time of 16 hours (range: 8-24 hrs) (FIGS. 6 and 8). Xerisol PLGA levothyroxine formulations XS-3, XS-8, and XS-9 reached Cmax faster at a median post-time of 8 hours (range: 8-24 hrs) (FIGS. 6 and 8), while PLGA levothyroxine formulations XS-2, XS-4, XS-5, XS-6, and XS-7 reached Cmax slower at a median post-time of 24 hours (range: 24-24 hrs) (FIGS. 6 and 8). The number of animals in each group was small (n=4) and Tmax range (FIG. 7) overlapped for all groups, these differences are considered insignificant.

As shown in FIG. 8, mean±SD baseline adjusted levothyroxine Cmax was highest for Xerisol levothyroxine (XS-1) (1784.2±527.1 ng/mL) and XeriSol levothyroxine PLGA formulations XS-2 (1750.1±389.7) and XS-9 (1789.3±386.1 ng/ml). XS-8 Cmax was about 10% lower than XS-1 and the remaining formulations had a Cmax that ranged between 27% and 50% lower than XS-1 in the following rank order: XS-7 (1305.9±305.9 ng/ml)>XS-4 (1156.9±69.8 ng/ml) >XS-3 (1130.3±504.2 ng/ml)>XS-5 (1011.2±227.2 ng/ml) >XS-6 (896.6±166.2 ng/mL).

Figure 9:
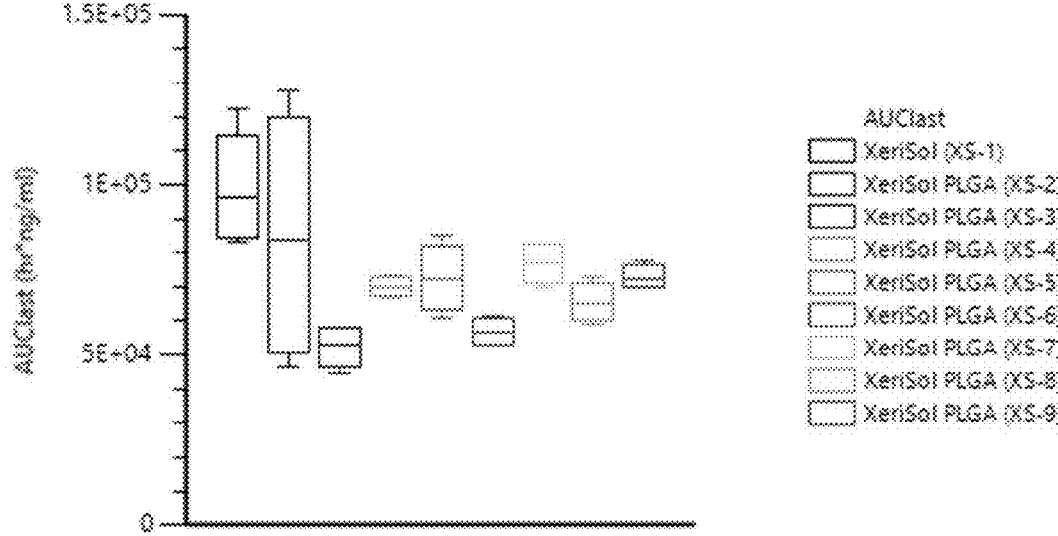
FIG. 9 is a box plot showing mean AUClast (hr*ng/ml) for levothyroxine formulations of the present invention administered subcutaneously to minipigs.

Results depicted in FIG. 9 demonstrate that the mean±SD baseline adjusted plasma levothyroxine exposure, as determined by AUClast (hr*ng/mL) was highest for Xerisol levothyroxine (XS-1) (96461.3±17426.8) followed by XS-2 (83732.2±36156.9). Five formulations had an AUClast that ranged between 20% and 32% lower than XS-1 in the following rank order: XS-7, XS-9, XS-5, XS-4, XS-8. Formulations XS-6 (56709.6±3976.1) and XS-3 (52934.8±6383.5) had the lowest exposure levels and were 41% and 45% lower, respectively, compared to formulation XS-1.

Figure 10:
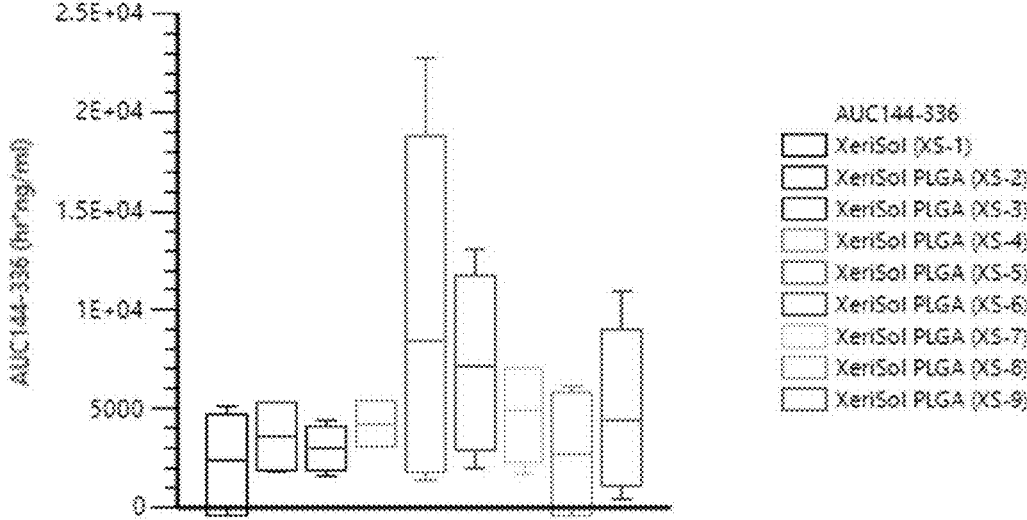
FIG. 10 is a box plot showing mean AUC144-336 (hr*ng/ml) for levothyroxine formulations of the present invention administered subcutaneously to minipigs.

As shown in FIG. 10, the mean±SD baseline adjusted plasma levothyroxine partial exposure (AUC144-336) was higher in all PLGA containing formulations compared to XS-1. Formulations XS-2 (3655.1±1903.9), XS-3 (3075.3±1182.2), and XS-8 (2721.3±3325.6) had an AUC144-336 that ranged between 12% and 50% greater than XS-1 (2435.8±2710.5). Formulations XS-4 (4237.9±1266.5), XS-7 (4938.8±2515.6), and XS-9 (4472.6±4503.2) had an AUC144-336 that ranged between 74% and 103% greater than XS-1. Formulations XS-5 (8467.0±9782.1) and XS-6 (7161.6±4582.0) had partial exposures that ranged between 194% and 248% greater than that of formulation XS-1.

These results are depicted in further comparison detail in Table 3 below, which compiles all of the measured and calculated pharmacokinetic parameters for each of the formulations.

32

TABLE 3

Pharmacokinetic Parameters of Baseline Adjusted Plasma Levothyroxine after Subcutaneous Administration of XeriSol ™ Levothyroxine and XeriSol/PLGA Levothyroxine Formulations in Göttingen Minipigs

| Group | | $C_{max}$ (ng/ml) | $AUC_{last}$ (hr*ng/ml) | $AUC_{144\text{-}336}$ (hr*ng/ml) | | $T_{max}$ (hr) |
|---|---|---|---|---|---|---|
| XeriSol | N | 4 | 4 | 4 | N | 4 |
| (XS-1) | Mean | 1784.2 | 96461.3 | 2435.8 | Min | 8 |
| | SD | 527.1 | 17426.8 | 2710.5 | Median | 16 |
| | CV % | 29.5 | 18.1 | 111.3 | Max | 24 |
| XeriSol | N | 4 | 4 | 4 | N | 4 |
| PLGA | Mean | 1750.1 | 83732.2 | 3655.1 | Min | 24 |
| (XS-2) | SD | 389.7 | 36156.9 | 1903.9 | Median | 24 |
| | CV % | 22.3 | 43.2 | 52.1 | Max | 24 |
| XeriSol | N | 4 | 4 | 4 | N | 4 |
| PLGA | Mean | 1130.3 | 52934.8 | 3075.3 | Min | 8 |
| (XS-3) | SD | 504.2 | 6383.5 | 1182.2 | Median | 24 |
| | CV % | 44.6 | 12.1 | 38.4 | Max | 24 |
| XeriSol | N | 4 | 4 | 4 | N | 4 |
| PLGA | Mean | 1156.9 | 70009.4 | 4237.9 | Min | 24 |
| (XS-4) | SD | 69.8 | 2854.5 | 1266.5 | Median | 24 |
| | CV % | 6.0 | 4.1 | 29.9 | Max | 24 |
| XeriSol | N | 4 | 4 | 4 | N | 4 |
| PLGA | Mean | 1011.2 | 72290.8 | 8467.0 | Min | 24 |
| (XS-5) | SD | 227.2 | 9952.8 | 9782.1 | Median | 24 |
| | CV % | 22.5 | 13.8 | 115.5 | Max | 24 |
| XeriSol | N | 4 | 4 | 4 | N | 4 |
| PLGA | Mean | 896.6 | 56709.6 | 7161.6 | Min | 24 |
| (XS-6) | SD | 166.2 | 3976.1 | 4582.0 | Median | 24 |
| | CV % | 18.5 | 7.0 | 64.0 | Max | 24 |
| XeriSol | N | 4 | 4 | 4 | N | 4 |
| PLGA | Mean | 1305.9 | 77093.9 | 4938.8 | Min | 24 |
| (XS-7) | SD | 305.9 | 6048.0 | 2515.6 | Median | 24 |
| | CV % | 23.4 | 7.8 | 50.9 | Max | 24 |
| XeriSol | N | 4 | 4 | 4 | N | 4 |
| PLGA | Mean | 1599.2 | 65309.6 | 2721.3 | Min | 8 |
| (XS-8) | SD | 401.4 | 5724.8 | 3325.6 | Median | 8 |
| | CV % | 25.1 | 8.8 | 122.2 | Max | 24 |
| XeriSol | N | 4 | 4 | 4 | N | 4 |
| PLGA | Mean | 1789.3 | 72445.4 | 4472.6 | Min | 8 |
| (XS-9) | SD | 386.1 | 3765.0 | 4503.2 | Median | 8 |
| | CV % | 21.6 | 5.2 | 100.7 | Max | 24 |

Formulations containing PLGA are anticipated to have a lower maximum concentration due to an expected slower drug release as PLGA degrades. A lower Cmax was prominently observed in formulations XS-3 through XS-7. A longer Tmax might also have been expected but was observed not to be materially different between formulations. Exposure was lower across all formulations containing PLGA from 10% to 45% relative to XeriSol™ levothyroxine (XS-1) without PLGA. These results suggest either incomplete or very slow absorption of the test articles containing PLGA. The partial exposure AUC144-336 shown in Table 3 and FIG. 10 demonstrate that PLGA-containing formulations have greater partial exposures over 144 hr through 336 hr compared to XS-1, suggesting that PLGA-containing formulations may have a slow, extended absorption.

Figure 11A:
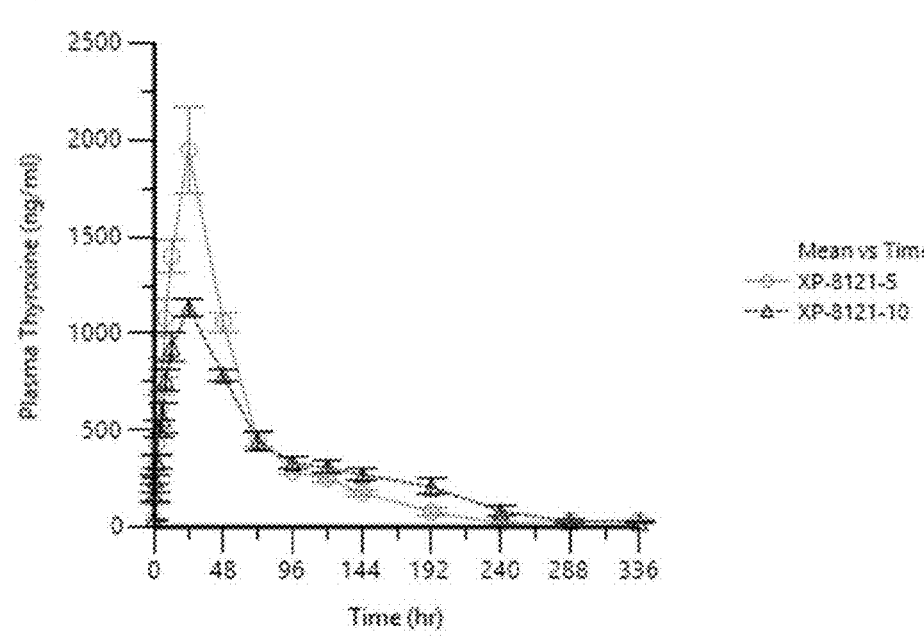
FIGS. 11A-11B are a pair of line graphs showing mean baseline-unadjusted plasma levothyroxine concentration in minipigs dosed with a 5 mg/mL levothyroxine formulation or a 10 mg/mL levothyroxine formulation of the present invention (XP-8121-5 and XP-8121-10, respectively), plotted on a linear scale (FIG. 11A) or a logarithmic scale (FIG. 11B).
Figure 11B:
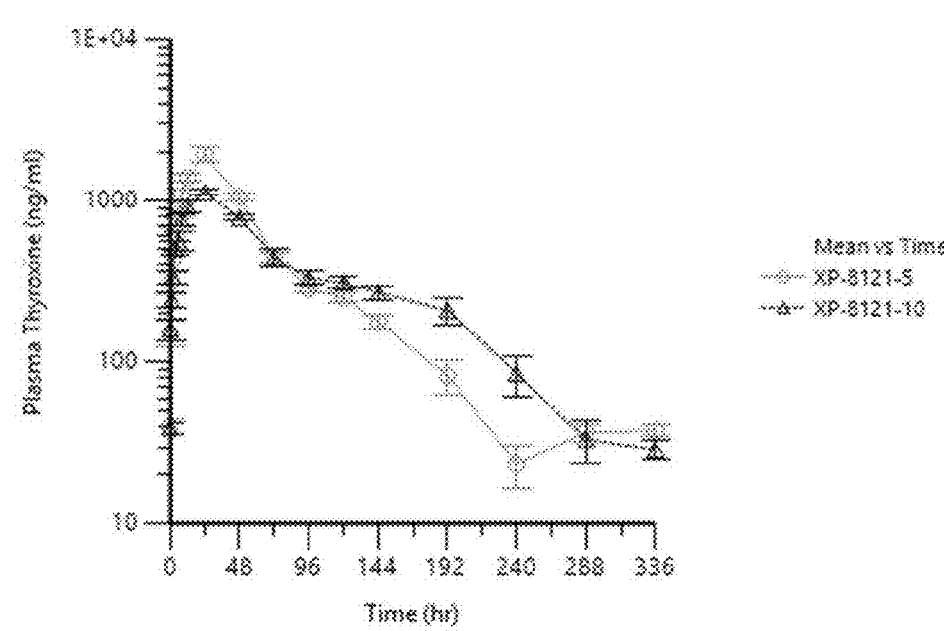
Figure 12A:
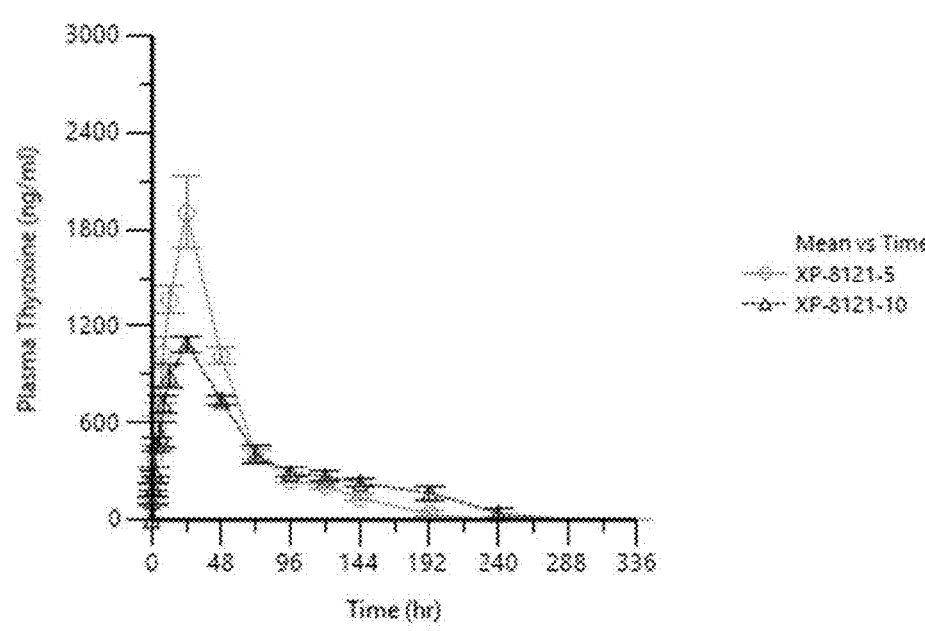
FIGS. 12A-12B are a pair of line graphs showing mean baseline-adjusted plasma levothyroxine concentration in minipigs dosed with a 5 mg/mL levothyroxine formulation or a 10 mg/mL levothyroxine formulation of the present invention (XP-8121-5 and XP-8121-10, respectively), plotted on a linear scale (FIG. 12A) or a logarithmic scale (FIG. 12B).
Figure 12B:
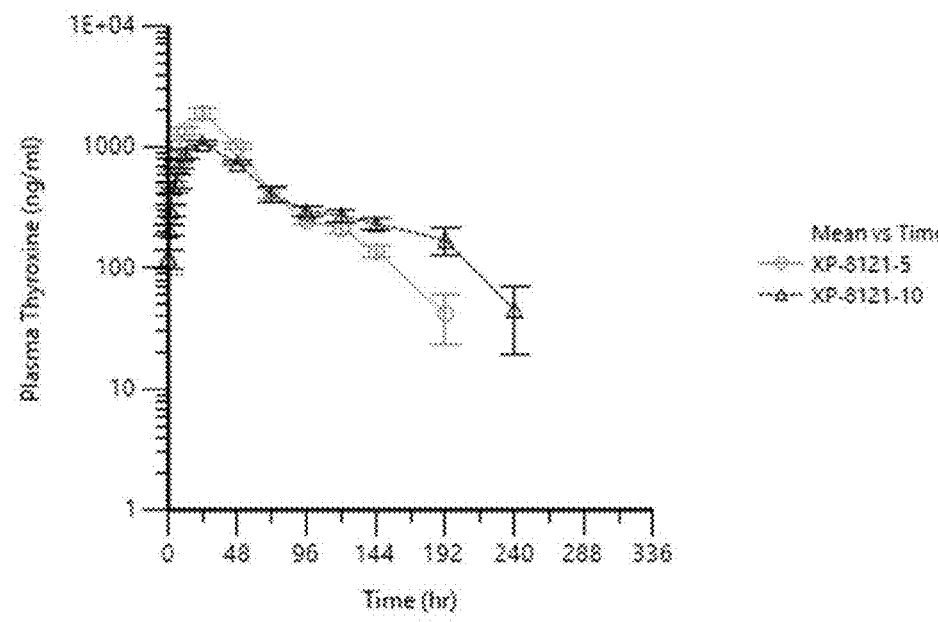

The inventors next wished to examine the pharmacokinetics in two Xerisol™ levothyroxine formulations comprising either 5 mg/mL ("XP-8121-5") or 10 mg/ml ("XP-8121-10") levothyroxine sodium. These formulations were prepared using the acidified DMSO solution approaches described in Example 1 above, where sulfuric acid was added to the formulation at a molar ratio of approximately 2.5-to-1 relative to the API content in a DMSO-based solvent system. Minipigs were dosed with the formulations as described in the preceding section, and pharmacokinetic parameters determined as described above. Results are shown in FIGS. 11 and 12. In both baseline-noncorrected (FIG. 11) and baseline-corrected (FIG. 12) analyses, both the 5 mg/mL and the 10 mg/mL formulations had a similar Tmax (within about 2 hours), whether that was assessed on a linear (FIGS. 11A and 12A) or semi-logarithmic (FIGS. 11B and 12B) plot. Interestingly, the Cmax for the 5 mg/mL 5 formulation was observed in all analyses to be higher than that for the 10 mg/mL formulation, although injection of the 10 mg/mL formulation led to sustained levothyroxine plasma concentrations for a longer period of time as compared to 5 mg/mL formulations. Individual and summary 10 baseline-unadjusted or baseline-adjusted pharmacokinetic parameters, determined as described above, are shown in Tables 4 and 5, respectively.

TABLE 4

Individual and Summary of Baseline-Unadjusted Plasma Levothyroxine Pharmacokinetic Parameters by Treatment

| Group | Subject | Lambda_z (1/hr) | Tmax (hr) | Cmax (ng/ml) | AUClast (hr*ng/ml) | Cl/F (ml/hr/kg) | Vz/F (ml/kg) | AUCINF (hr*ng/ml) | Half_life (hr) |
|---|---|---|---|---|---|---|---|---|---|
| XP-8121-5 | 801.00 | 0.02 | 24.00 | 1610.00 | 102921.49 | 4.72 | 298.37 | 105910.92 | 43.81 |
| | 802.00 | 0.01 | 24.00 | 1620.00 | 116348.25 | 4.20 | 309.50 | 119030.16 | 51.07 |
| | 803.00 | 0.01 | 8.00 | 1320.00 | 100939.86 | 4.83 | 386.93 | 103618.07 | 55.58 |
| | 804.00 | 0.02 | 24.00 | 2020.00 | 116504.71 | 4.22 | 223.21 | 118375.40 | 36.63 |
| | 805.00 | 0.02 | 24.00 | 2680.00 | 123289.00 | 3.97 | 216.96 | 125816.76 | 37.84 |
| | 806.00 | 0.01 | 24.00 | 2450.00 | 119332.28 | 4.12 | 290.40 | 121304.97 | 48.83 |
| | N | 6 | 6 | 6 | 6 | 6 | 6 | 6 | 6 |
| | Mean | 0.016 | 21.333 | 1950.000 | 113222.598 | 4.344 | 287.561 | 115676.047 | 45.627 |
| | SD | 0.003 | 6.532 | 530.886 | 9123.388 | 0.345 | 62.619 | 8874.770 | 7.535 |
| | Min | 0.01 | 8.00 | 1320.00 | 100939.86 | 3.97 | 216.96 | 103618.07 | 36.63 |
| | Median | 0.02 | 24.00 | 1820.00 | 116426.48 | 4.21 | 294.38 | 118702.78 | 46.32 |
| | Max | 0.02 | 24.00 | 2680.00 | 123289.00 | 4.83 | 386.93 | 125816.76 | 55.58 |
| | Geometric Mean | 0.015 | 19.984 | 1890.578 | 112908.263 | 4.333 | 281.961 | 115385.695 | 45.102 |
| | Geometric CV % | 16.87 | 47.20 | 27.79 | 8.24 | 7.83 | 21.99 | 7.83 | 16.87 |
| XP-8121-10 | 801.00 | | 24.00 | 1130.00 | 108173.71 | | | | |
| | 802.00 | 0.01 | 24.00 | 1040.00 | 120036.18 | 4.07 | 345.80 | 122874.53 | 58.90 |
| | 803.00 | | 24.00 | 1150.00 | 112914.56 | | | | |
| | 804.00 | | 24.00 | 1310.00 | 88043.36 | | | | |
| | 805.00 | 0.01 | 24.00 | 963.00 | 93515.73 | 5.20 | 524.08 | 96166.74 | 69.87 |
| | 806.00 | 0.01 | 24.00 | 1180.00 | 90859.16 | 5.39 | 379.21 | 92744.24 | 48.76 |
| | N | 3 | 6 | 6 | 6 | 3 | 3 | 3 | 3 |
| | Mean | 0.012 | 24.000 | 1128.833 | 102257.117 | 4.887 | 416.365 | 103928.506 | 59.176 |
| | SD | 0.002 | 0.000 | 119.399 | 13213.919 | 0.714 | 94.771 | 16496.738 | 10.559 |
| | Min | 0.01 | 24.00 | 963.00 | 88043.36 | 4.07 | 345.80 | 92744.24 | 48.76 |
| | Median | 0.01 | 24.00 | 1140.00 | 100844.72 | 5.20 | 379.21 | 96166.74 | 58.90 |
| | Max | 0.01 | 24.00 | 1310.00 | 120036.18 | 5.39 | 524.08 | 122874.53 | 69.87 |
| | Geometric Mean | 0.012 | 24.000 | 1123.565 | 101552.115 | 4.850 | 409.609 | 103099.822 | 58.544 |
| | Geometric CV % | 18.14 | 0.00 | 10.64 | 12.92 | 15.39 | 22.10 | 15.39 | 18.14 |

45

TABLE 5

Individual and Summary of Baseline-Adjusted Plasma Levothyroxine Pharmacokinetic Parameters by Treatment

| Group | Subject | Tmax (hr) | Cmax (ng/ml) | AUClast (hr*ng/ml) | AUCINF (hr*ng/ml) | Half_life (hr) | Vz/F (ml/kg) | Cl/F (ml/hr/kg) | Lambda_z (1/hr) |
|---|---|---|---|---|---|---|---|---|---|
| XP-8121-5 | 801.00 | 24.00 | 1563.30 | 87576.73 | 87600.43 | 27.83 | 225.50 | 5.71 | 0.03 |
| | 802.00 | 24.00 | 1564.60 | 98858.82 | 104601.05 | 48.19 | 332.30 | 4.78 | 0.01 |
| | 803.00 | 8.00 | 1276.10 | 86833.97 | 87255.59 | 35.21 | 291.09 | 5.73 | 0.02 |
| | 804.00 | 24.00 | 1995.80 | 108576.29 | 109342.48 | 47.42 | 312.82 | 4.57 | 0.01 |
| | 805.00 | 24.00 | 2643.60 | 111912.97 | 112568.74 | 45.91 | 294.22 | 4.44 | 0.02 |
| | 806.00 | 24.00 | 2414.30 | 108161.05 | 113306.72 | 53.80 | 342.49 | 4.41 | 0.01 |
| | N | 6 | 6 | 6 | 6 | 6 | 6 | 6 | 6 |
| | Mean | 21.333 | 1909.617 | 100319.971 | 102445.837 | 42.985 | 299.736 | 4.941 | 0.017 |
| | SD | 6.532 | 536.876 | 11049.382 | 12031.377 | 9.757 | 41.656 | 0.617 | 0.005 |
| | Min | 8.00 | 1276.10 | 86833.97 | 87255.59 | 27.38 | 225.50 | 4.41 | 0.01 |
| | Median | 24.00 | 1780.20 | 103509.94 | 106971.77 | 46.67 | 303.52 | 4.68 | 0.01 |
| | Max | 24.00 | 2643.60 | 111912.97 | 113306.72 | 53.80 | 342.49 | 5.73 | 0.03 |
| | Geometric Mean | 19.984 | 1847.449 | 99799.880 | 101831.701 | 41.940 | 297.088 | 4.910 | 0.017 |
| | Geometric CV % | 47.20 | 28.80 | 11.28 | 12.19 | 25.58 | 15.05 | 12.19 | 25.58 |

TABLE 5-continued

| | | | | | | | | | |
|---|---|---|---|---|---|---|---|---|---|
| | Individual and Summary of Baseline-Adjusted Plasma Levothyroxine Pharmacokinetic Parameters by Treatment |
| Group | Subject | Tmax (hr) | Cmax (ng/ml) | AUClast (hr*ng/ml) | AUCINF (hr*ng/ml) | Half_life (hr) | Vz/F (ml/kg) | Cl/F (ml/hr/kg) | Lambda_z (1/hr) |
| XP-8121-10 | 801.00 | 24.00 | 1092.00 | 95259.58 | | | | | |
| | 802.00 | 24.00 | 995.50 | 104461.74 | 106291.35 | 37.63 | 255.39 | 4.70 | 0.02 |
| | 803.00 | 24.00 | 1121.20 | 103386.88 | 103851.02 | 30.64 | 212.82 | 4.81 | 0.02 |
| | 804.00 | 24.00 | 1258.90 | 73496.99 | 74683.68 | 34.71 | 335.22 | 6.69 | 0.02 |
| | 805.00 | 24.00 | 921.70 | 80464.98 | 81734.06 | 34.23 | 302.08 | 6.12 | 0.02 |
| | 806.00 | 24.00 | 1145.80 | 79862.21 | 80056.53 | 29.93 | 269.71 | 6.25 | 0.02 |
| | N | 6 | 6 | 6 | 5 | 5 | 5 | 5 | 5 |
| | Mean | 24.000 | 1089.183 | 89488.730 | 89323.328 | 33.428 | 275.044 | 5.715 | 0.021 |
| | SD | 0.000 | 118.211 | 13270.162 | 14635.212 | 3.160 | 46.472 | 0.900 | 0.002 |
| | Min | 24.00 | 921.70 | 73496.99 | 74683.68 | 29.93 | 212.82 | 4.70 | 0.02 |
| | Median | 24.00 | 1106.60 | 87862.28 | 81734.06 | 34.23 | 269.71 | 6.12 | 0.02 |
| | Max | 24.00 | 1258.90 | 104461.74 | 106291.35 | 37.63 | 335.22 | 6.69 | 0.02 |
| | Geometric Mean | 24.000 | 1083.776 | 88666.219 | 88386.685 | 33.309 | 271.840 | 5.657 | 0.021 |
| | Geometric CV % | 0.00 | 11.01 | 14.99 | 16.26 | 9.47 | 17.37 | 16.26 | 9.47 |

Taken together, these results indicate that the liquid injectable levothyroxine-containing formulations of the present invention are storage stable and provide ready-to-use therapeutic formulations that rapidly increase plasma levothyroxine concentrations in subjects into whom the formulations have been subcutaneously injected. Moreover, these results indicate that compared to oral daily doses of levothyroxine, which show rapid plasma concentration increases followed by rapid decreases of levothyroxine from the plasma, the formulations of the present invention provide a means of more slowly reaching therapeutic levels of levothyroxine in the plasma, with a subsequent sustained concentration. Thus, the present formulations should provide a way of treating patients with hypothyroidism on a once weekly (or perhaps even once every other week, using even higher concentration levothyroxine formulations (e.g., 15 mg/mL, 20 mg/mL, 40 mg/mL, etc.) of the invention) treatment schedule, thereby improving the patient experience with their medication and patient compliance with the treatment regimen while retaining a robust pharmacokinetic (and presumably efficacy) profile.

Example 3: Human Pharmacokinetic Studies Using Liquid Levothyroxine-Containing Formulations In another set of studies, the present inventors wished to determine whether the pharmacokinetics observed in humans using the XP-8121 levothyroxine-containing formulations of the invention would be similar to those observed in pre-clinical studies using laboratory animals as described in Example 2. These studies were designed for several purposes: (a) to characterize the pharmacokinetics of XP-8121 subcutaneous injection (at doses of 600 µg, 1200 µg, and 1500 µg from the 10 mg/mL formulation of levothyroxine described in Example 2 as XP-8121); (b) to evaluate XP-8121 bioavailability (relative to oral levothyroxine formulations such as Synthroid®) and dose proportionality (600 µg, 1200 µg, and 1500 µg); and (c) to assess the safety and tolerability of XP-8121. Post-study PK analyses (population PK modeling) were also conducted to compare steady state exposure (AUC) between weekly subcutaneous (SC) dosing of XP-8121 and daily oral (PO) dosing of Synthroid®, and to examine dose conversion from Synthroid® PO to XP-8121 SC.

Figure 13:
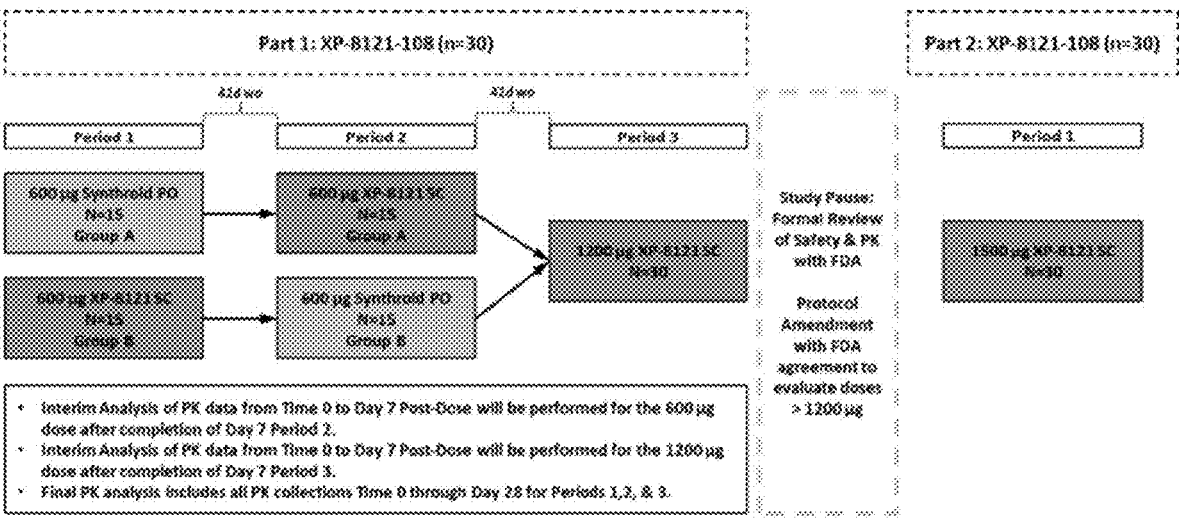
FIG. 13 is a graphic depiction of the study design for a human clinical trial, designated XP-8121-108, to determine the pharmacokinetics of subcutaneous (SC) administration of certain levothyroxine-containing formulations of the invention vs. oral (PO) administration of a tablet dosage form (Synthroid®).

The study was designed according to the schematic shown in FIG. 13. The study, designated XP-8121-108, examined plasma levothyroxine pharmacokinetics in 30 subjects, divided equally into two groups of 15, who received 600 µg of either Synthroid® PO or XP-8121 SC on day 0, followed by a 42-day washout period after which the subjects received 600 µg of the other form of levothyroxine, and then after another 42-day washout period, both groups received a subcutaneous injection of 1200 µg of XP-8121. Following a brief study pause for review of safety and pharmacokinetic data with the US FDA, the protocol for the study was amended to evaluate doses above 1200 µg of levothyroxine. Therefore, in the final portion of the study, 30 additional subjects received a subcutaneous injection of 1500 µg of levothyroxine in the XP8121 formulation of the invention. Pharmacokinetic parameters were measured and determined as noted in FIG. 13, and calculations were performed as described for preclinical pharmacokinetic analyses in Example 2. Results of these studies are shown in FIGS. 14-18.

FIG. 14 demonstrates the mean baseline-adjusted plasma levothyroxine concentrations over time, plotted on a linear plot (FIG. 14A) and a logarithmic plot (FIG. 14B), for various doses (600 µg, 1200 µg, 1500 µg) of XP-8121 injected subcutaneously (SC) vs. orally administered 600 µg (PO) Synthroid®. As seen in FIGS. 14A and 14B, Synthroid® PO 600 µg exhibited a rapid rise in levothyroxine levels followed by a rapid decline, while XP-8121 SC (all doses) exhibited a slower rise in levothyroxine levels followed by a sustained exposure that stayed above levothyroxine levels obtained from Synthroid® PO. Moreover, once Cmax was reached, plasma T4 levels remained stably elevated over 4-5 days with XP-8121, as opposed to Synthroid® which immediately dropped. Finally, the Tmax for XP-8121 was also seen to be longer than that of Synthroid® PO.

Figure 15A:
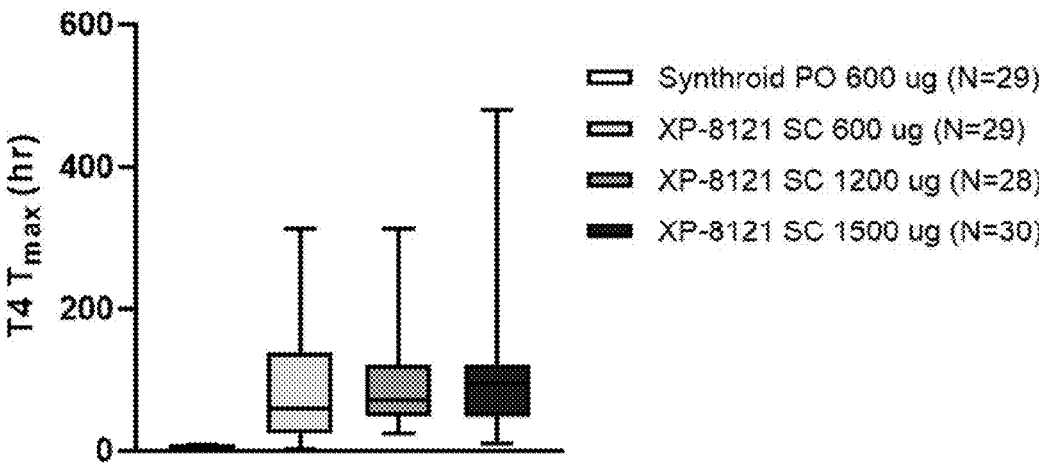
FIGS. 15A-15B are a pair of box plots showing mean baseline-adjusted Tmax (in hours) (FIG. 15A) or mean baseline-adjusted half-life ($T_{1/2}$, in hours) (FIG. 15B) for levothyroxine formulations of the present invention administered subcutaneously to human subjects in the XP-8121-108 clinical study.
Figure 15B:
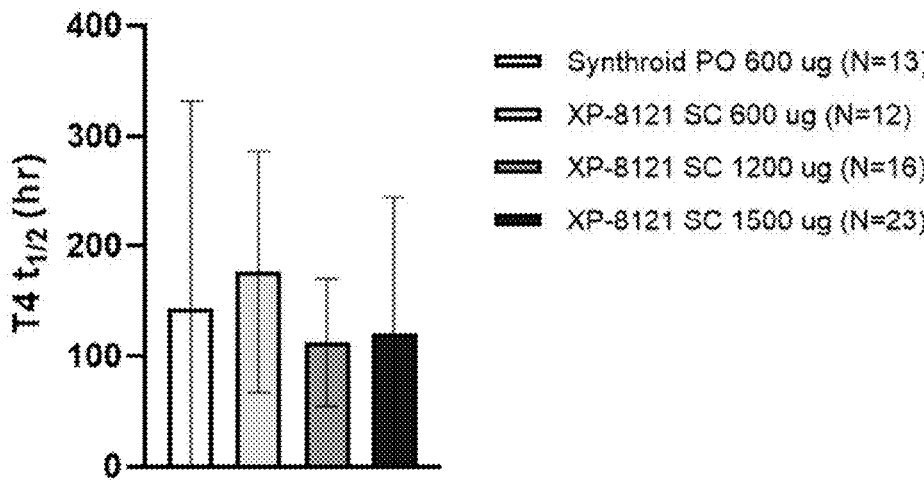
Figure 16A:
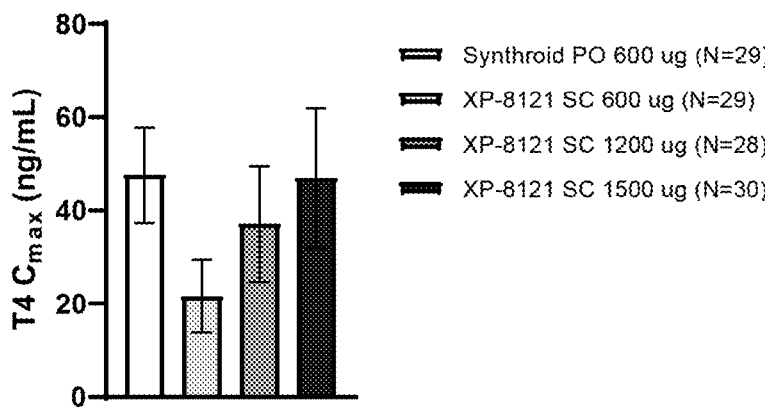
FIGS. 16A-16B are a pair of box plots showing mean baseline-adjusted Cmax (ng/mL) (FIG. 16A) or mean baseline-adjusted AUClast (ng*hr/mL) (FIG. 16B) for levothyroxine formulations of the present invention administered subcutaneously to human subjects in the XP-8121-108 clinical study.

Similar results were seen for other pharmacokinetic parameters. As shown in FIG. 15A, the median Tmax for XP-8121 (48, 72, 96 hours for the 600 µg, 1200 µg and 1500 µg doses, respectively) was greater than that observed for Synthroid® PO (3 hours). As shown in FIG. 15B, the mean half-life ($T_{1/2}$) for XP-8121 (177, 112, and 120 hours for the 600 µg, 1200 µg and 1500 µg doses, respectively) was similar to that observed for Synthroid® PO (144 hours). FIG. 16 shows the mean baseline levothyroxine exposure in subjects treated with SC XP-8121 vs. PO Synthroid®. The mean Cmax of XP-8121 600 µg was lower than the mean Cmax of Synthroid® PO 600 µg (FIG. 16A). Moreover, while the mean unadjusted levothyroxine AUClast values were similar between XP-8121 SC 600 µg and Synthroid®

Figure 16B:
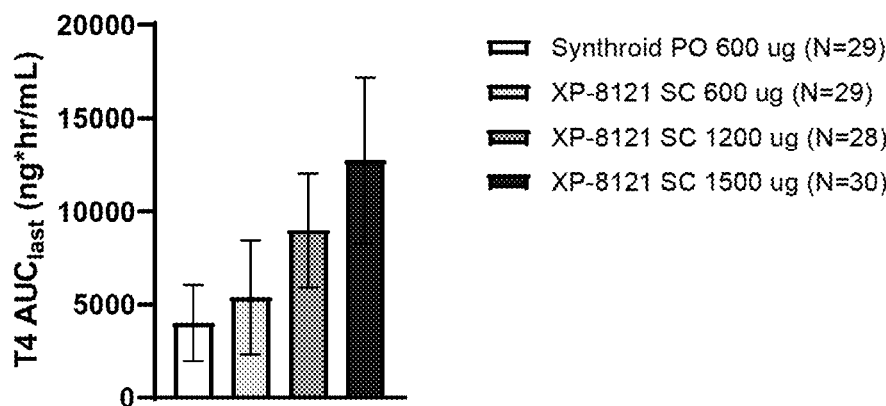

PO 600 μg (data not shown), the mean baseline-adjusted levothyroxine AUClast with XP-8121 SC 600 μg was 35% greater than that of Synthroid® PO 600 μg (FIG. 16B). XP-8121 SC also showed dose-dependent increases in exposure (Cmax (FIG. 16A) and AUClast (FIG. 16B)). Thus, single dose SC XP-8121 has significantly lower Cmax, with similar or greater exposure as determined by AUClast, compared to Synthroid® PO.

Figure 17A:
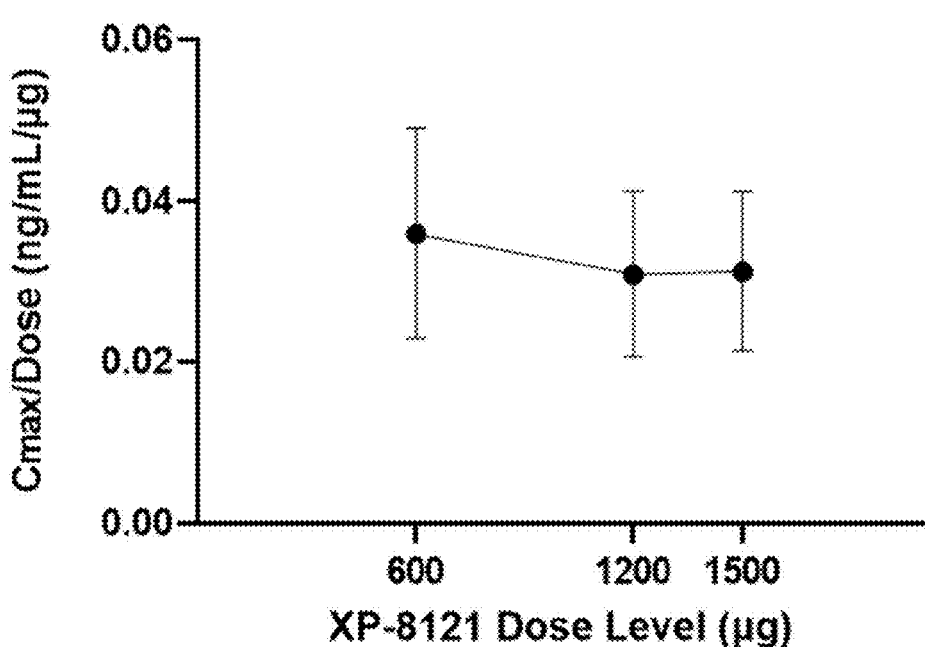
FIGS. 17A-17B are a pair of line graphs showing the mean baseline-adjusted Cmax normalized to levothyroxine dose in human subjects in the XP-8121-108 study, dosed with a 10 mg/mL levothyroxine formulation of the present invention (XP-8121) subcutaneously (SC) at 600 µg, 1200 µg or 1500 µg. Results are plotted on a linear scale (FIG. 17A) or a logarithmic scale (FIG. 17B).
Figure 17B:
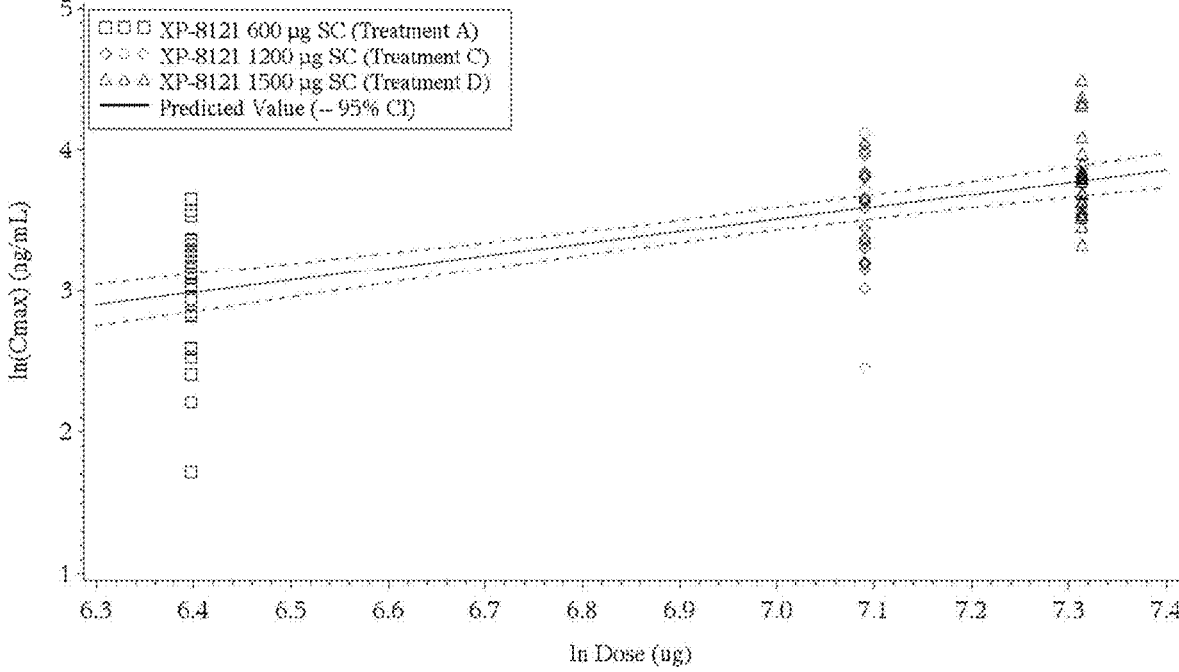
Figure 18A:
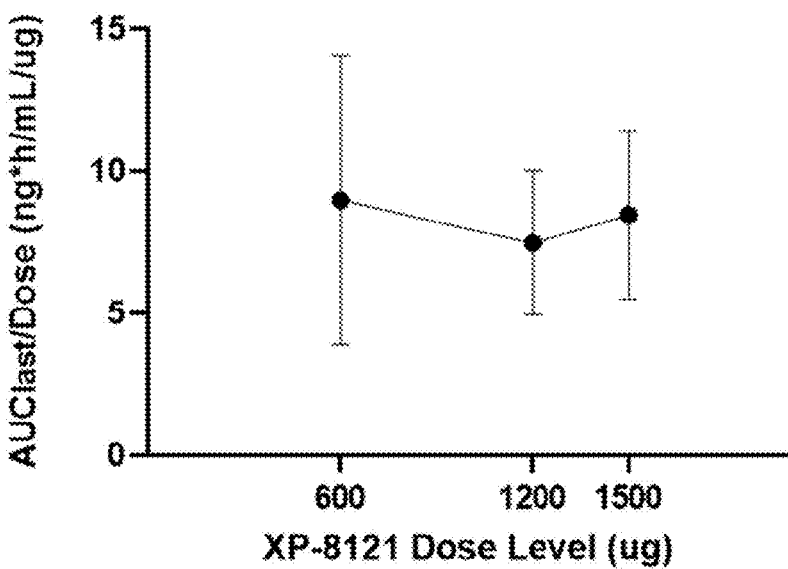
FIGS. 18A-18B are a pair of line graphs showing the mean baseline-adjusted AUClast normalized to levothyroxine dose in human subjects in the XP-8121-108 study, dosed with a 10 mg/mL levothyroxine formulation of the present invention (XP-8121) subcutaneously (SC) at 600 µg, 1200 µg, or 1500 µg. Results are plotted on a linear scale (FIG. 18A) or a logarithmic scale (FIG. 18B).
Figure 18B:
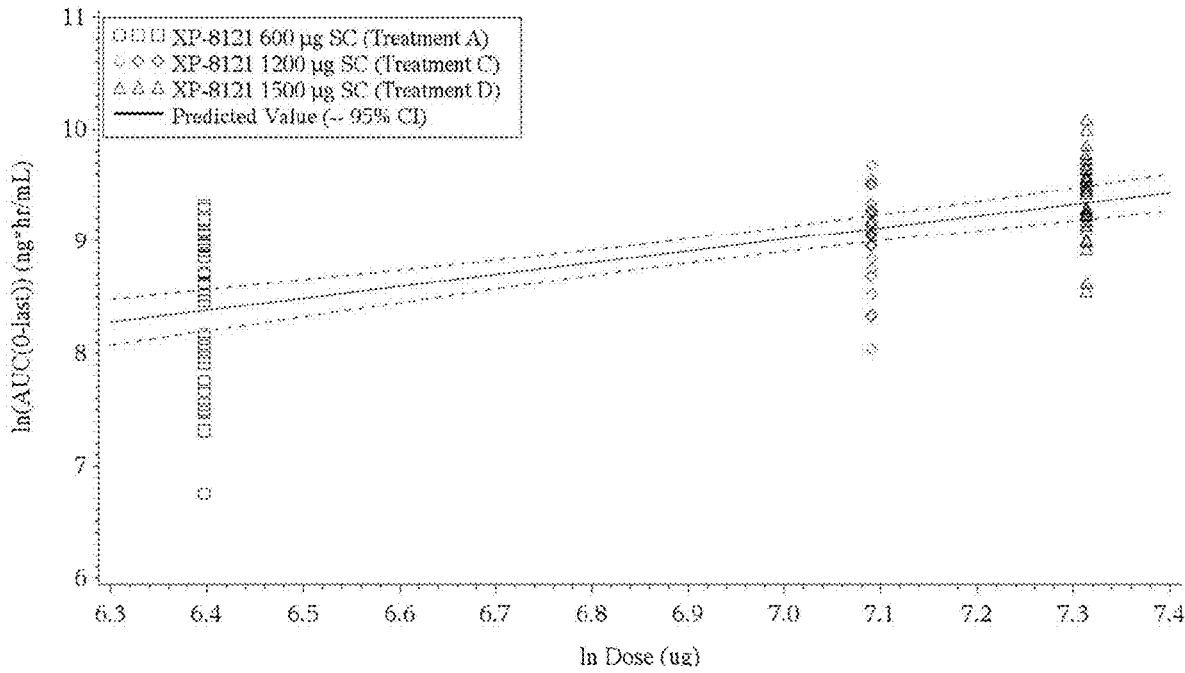

To further examine the dose proportionality of baseline adjusted XP-8121, the mean baseline-adjusted Cmax normalized to levothyroxine dose was plotted on a linear scale (FIG. 17A) or a logarithmic scale (FIG. 17B). These parameters were calculated using concentrations from matched PK timepoints for Parts 1 and 2 of the Study (PK Population) as set forth in FIG. 13. The results shown in FIG. 17 demonstrate that baseline-adjusted Cmax for XP-8121 is dose proportional. Similarly, baseline-adjusted AUClast for XP-8121 was also found to be dose proportional, whether plotted on a linear scale (FIG. 18A) or a logarithmic scale (FIG. 18B).

Figures 19A, 19B:
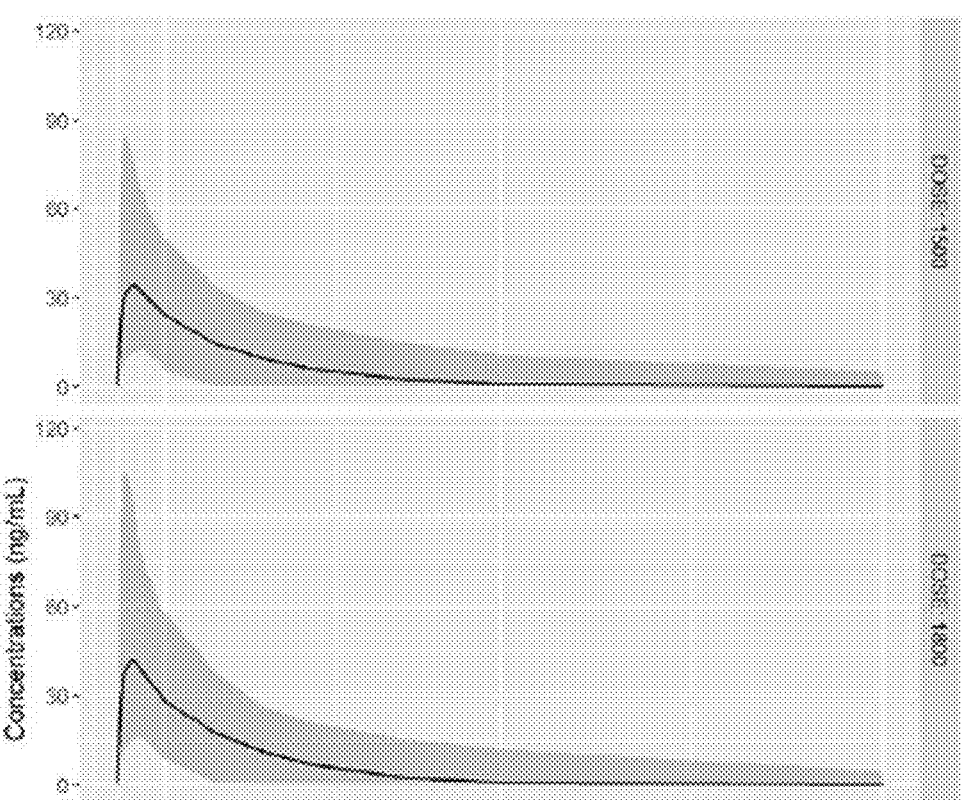
FIGS. 19A-19B is a pair of line graphs showing population pharmacokinetic (PPK) models of XP-8121 plasma levothyroxine concentrations based on the single dose results obtained in the XP-8121-108 study, for a 1500 µg dose of SC levothyroxine (FIG. 19A) or an 1800 µg dose of SC levothyroxine (FIG. 19B).
Figure 20:
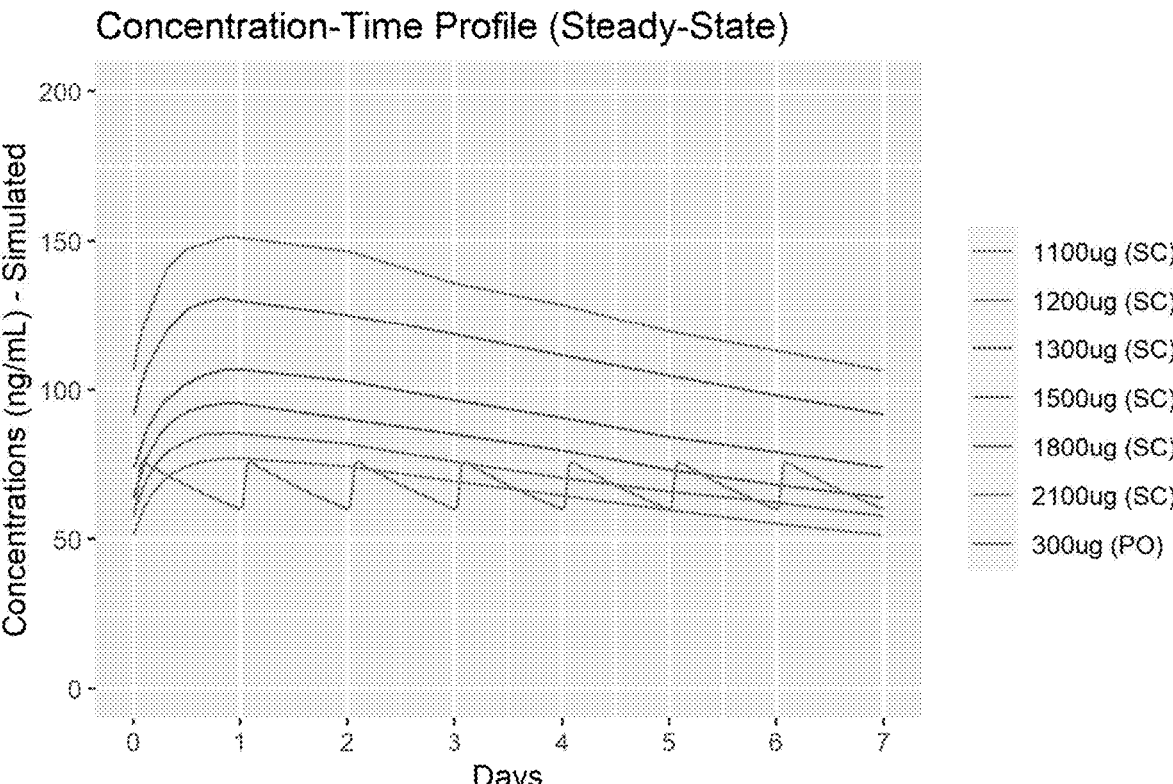
FIG. 20 is a line graph showing a simulated concentration-time profile (steady-state) for XP-8121 10 mg/mL levothyroxine administered subcutaneously to human subjects at doses of 1100 µg, 1200 µg, 1300 µg, 1500 µg, 1800 µg or 2100 µg, vs. Synthroid® PO at 300 µg. These simulated results are based on the PPK model described in FIG. 19.

Having demonstrated that the pharmacokinetics for the SC XP-8121 levothyroxine formulations of the present invention approximate or, in some cases are superior to, Synthroid® PO, these single-dose data were used to generate a population pharmacokinetic (PPK) model of XP-8121 to attempt to determine the conversion dose of XP-8121 from Synthroid® via PPK simulations. To prepare these PPK models, fixed- and random-effect parameters were estimated using the First Order Conditional Estimation (FOCE) method by the NONMEM software program. The simulations employed a 1-compartment disposition model with first order elimination, examining a single dose of XP-8121 at a time. Exemplary PPK model graphs are shown in FIG. 19 for a 1500 μg dose of XP-8121 (FIG. 19A) or an 1800 μg dose of XP-8121 (FIG. 19B). These models were then used to generate simulated concentration-time data at steady state for multiple doses and using this PPK model the present inventors were able to determine the dose conversion for once-weekly SC XP-8121 from daily Synthroid® PO. An example of the PPK simulated results for Synthroid® PO and multiple doses of XP-8121 SC at steady state is shown in the concentration-time profile depicted in FIG. 20. Examining other PK parameters through this model, the following simulated results were obtained:

TABLE 6

| Steady State AUC Over 168 Hours (ng*hr/mL) | | | |
|---|---|---|---|
| Formulation | Dose (μg) | GeoMean | GeoCv % |
| XP-8121 | 1100 | 10851 | 50.7 |
| XP-8121 | 1200 | 12020 | 51.1 |
| XP-8121 | 1300 | 13534 | 51.6 |
| Synthroid ® | 300 | 11732 | 42.1 |

TABLE 7

| Steady State Cmax (ng/mL) | | | |
|---|---|---|---|
| Formulation | Dose (μg) | GeoMean | GeoCv % |
| XP-8121 | 1200 | 86.6 | 40.6 |
| Synthroid ® | 300 | 78.6 | 37.8 |

TABLE 8

| Steady State Cmin (ng/mL) (Ctrough) | | | |
|---|---|---|---|
| Formulation | Dose (μg) | GeoMean | GeoCv % |
| XP-8121 | 1200 | 53.4 | 78.2 |
| Synthroid ® | 300 | 61.7 | 47.3 |

Based on these simulated exposure findings at steady-state, exposure from weekly XP-8121 1200 μg SC doses is predicted to overlap that of daily Synthroid® PO 300 μg doses. Thus, the conversion factor from Synthroid® PO to XP-8121 SC is about 4×.

Together with those of the preceding Examples, these results indicate that storage stable, ready-to-use injectable liquid levothyroxine-containing formulations can be produced as described herein, and that these formulations, when introduced subcutaneously into a subject (such as humans, as in this Example 3), can facilitate slower increases in plasma levothyroxine levels in the subject, with slower clearance kinetics than those observed for oral immediate release solid formulations of levothyroxine such as Synthroid®. More particularly, the results of this Example 3 demonstrated that while Synthroid® PO 600 μg exhibits a rapid rise in levothyroxine levels followed by a rapid decline, XP-8121 SC (all doses) exhibited a slower rise in levothyroxine levels followed by a sustained exposure. Moreover, for XP-8121 SC (all doses) the Tmax was longer than that for Synthroid® PO 600 μg. The plasma levothyroxine half-life was similar in all groups, while mean Cmax for XP-8121 600 μg was less than half (47%) of the Cmax of Synthroid® PO 600 μg. In addition, XP-8121 SC levothyroxine increases in exposure (Cmax and AUClast) were seen to be dose proportional. In the population pharmacokinetic simulated model, we showed that we were able to generate a population pharmacokinetic model from single-dose data and to generate simulated concentration-time data at steady state (multiple doses). Finally, exposure from weekly subcutaneous injections of 1200 μg of XP-8121 was seen to overlap that of Synthroid® PO at 300 μg and indicated a dose conversion factor for SC XP-8121 from Synthroid® PO of about 4×.

Example 4: Evaluating a Broad Range of Different Ionization Stabilizing Excipients Following on the initial observations described in Example 1 above where increasing chemical stability was observed as a function of added sulfuric acid, an additional study was performed to explore a broader range of stabilizing excipient concentrations. As described in this study, the excipient concentrations were based on a molar ratio relative to the API molar concentration. For example, if the API molar concentration is 5.0 mM, a 1× molar ratio of excipient would correspond to 5 mM excipient concentration, and 2× corresponds to mM excipient concentration, etc.

The non-limiting examples of ionization stabilizing excipients evaluated in this study were hydrochloric acid (HCl), sulfuric acid ($H_2SO_4$) and potassium hydroxide (KOH), with excipient concentrations ranging from 1-4× molar ratio (relative to API) in 1× molar ratio increments. To maintain a consistent moisture content across all samples, the respective HCl, $H_2SO_4$, and KOH stock solutions used to spike the samples were prepared at a similar 0.5 M concentration. No additional excipients (e.g., trehalose, etc.) were included in the formulations evaluated in this study. Two control formulations (Control 1 and Control 2) and 30 test formulations (Sample 1 through Sample 30) were pre-pared, according to the formulation criteria shown in Table 9.

TABLE 9

Formulation Criteria for Evaluating Ranges of
Different Ionization Stabilizing Excipients

| Sample No. | Stabilizing Excipient | Molar Ratio (x) |
|---|---|---|
| Control 1 | N/A | 0 |
| 1 | KOH | 3 |
| 2 | HCl | 2 |
| 3 | KOH | 4 |
| 4 | HCl | 3 |
| 5 | KOH | 1 |
| 6 | $H_2SO_4$ | 2 |
| 7 | HCl | 3 |
| 8 | KOH | 3 |
| 9 | $H_2SO_4$ | 1 |
| 10 | $H_2SO_4$ | 4 |
| 11 | $H_2SO_4$ | 3 |
| 12 | HCl | 1 |
| 13 | HCl | 4 |
| 14 | KOH | 2 |
| 15 | $H_2SO_4$ | 2 |
| 16 | KOH | 3 |
| 17 | HCl | 2 |
| 18 | KOH | 4 |
| 19 | HCl | 3 |
| 20 | KOH | 1 |
| 21 | $H_2SO_4$ | 2 |
| 22 | HCl | 3 |
| 23 | KOH | 3 |
| 24 | $H_2SO_4$ | 1 |
| 25 | $H_2SO_4$ | 4 |
| 26 | $H_2SO_4$ | 3 |
| 27 | HCl | 1 |
| 28 | HCl | 4 |
| 29 | KOH | 2 |
| 30 | $H_2SO_4$ | 2 |
| Control 2 | N/A | 0 |

A statistical software packaged (JMP, v16) was used to develop an experiment containing 30 randomized samples, shown in Table 9. Each combination of excipient type plus excipient concentration was replicate at least twice in the study, with each replicate sample prepared independently. In addition to the 30 samples containing an excipient, two additional samples were included in the study. These samples (Control 1 and Control 2) did not contain added HCl, $H_2SO_4$, or KOH, or any other excipient.

A levothyroxine sodium concentration of 5 mg/mL (corresponding to approximately 6.25 mM levothyroxine molar concentration) was prepared by dissolving the drug sub-stance powder directly in neat USP-grade DMSO. Once dissolved, this solution was filled into 2R ISO glass vials (1.0 mL fill volume per vial). The sample vials were then spiked with the required volume of HCl, $H_2SO_4$, or KOH to achieve the specified excipient concentration. Sample vials were then stored in an oven set to 45° C. for 17 days prior to analysis by RP-HPLC. Results are shown in FIG. 21.

Figure 21:
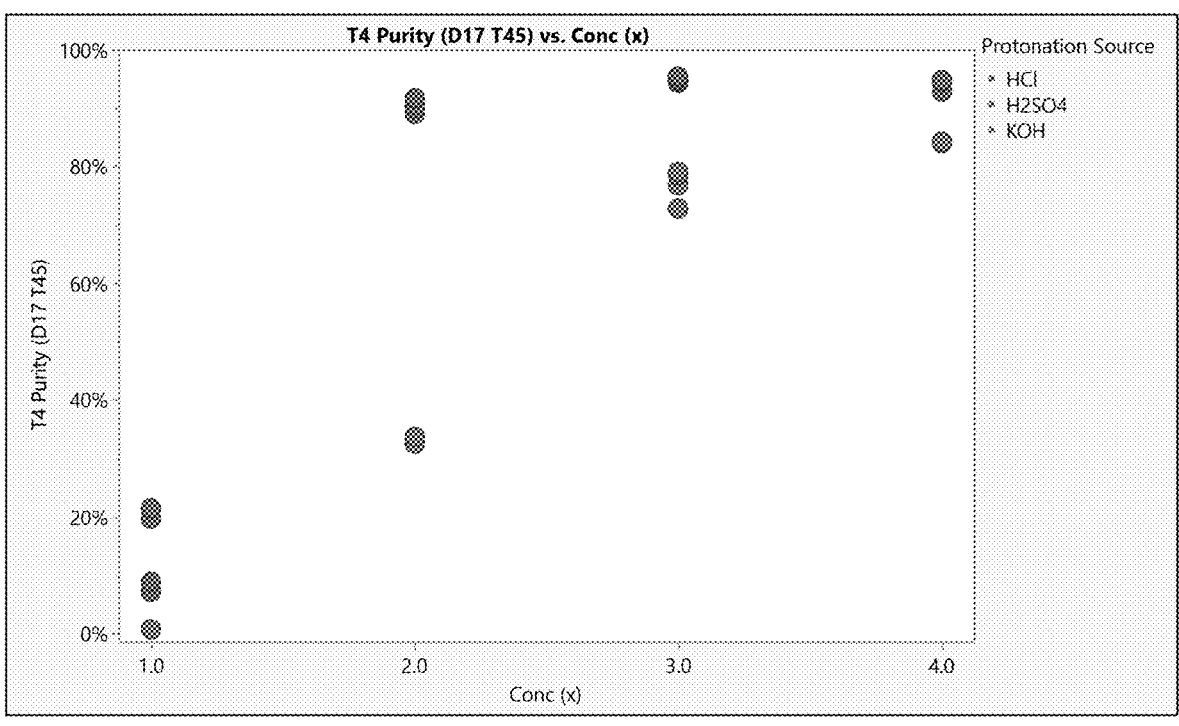
FIG. 21 is a scatter graph showing the levothyroxine peak purity (measured by RP-HPLC) of levothyroxine formulations of the invention prepared using different protonation sources, following 17 days of storage at 45° C.

The stability data (presented as the percent purity of levothyroxine peak relative to all measured peaks in the chromatogram) shown in FIG. 21 indicate poor chemical stability at 1x molar ratio of all excipients, which increases significantly at 2x for both mineral acids (HCl and $H_2SO_4$) evaluated in this study. For the two mineral acids, the chemical stability appears to remain relatively consistent across the range 2-4x molar concentration. Interestingly, although KOH did not promote chemical stability to the same extent as the mineral acids, it did indicate that increasing concentrations of KOH up to 4x molar ratio to API appeared to improve stability (though still below the level observed with the mineral acids). Additional studies were not performed at excipient concentration above 4x molar ratio.

Though not shown in the graph in FIG. 21, the two control samples (Control 1 and Control 2, containing only levothy-roxine dissolved in DMSO without any additional excipi-ents) did not have any detectable peak in their RP-HPLC chromatograms corresponding to the unmodified levothy-roxine molecule (i.e., levothyroxine peak purity was con-sidered to be approximately 0%). This result further supports observations of the studies described in Example 1 that direct dissolution of levothyroxine in DMSO without any stabilizing excipient appears to produce a chemically unstable formulation.

In general, formulation excipients are added at the lowest concentration required to promote physical and/or chemical stability. Therefore, while KOH also appeared in this study to have the ability to promote API stability, the two mineral acids evaluated in this study (HCl and $H_2SO_4$), were capable of promoting stability to a higher extent at much lower concentrations and would therefore probably be more appro-priate as potential ionization stabilizing excipients in a commercial drug product.

Example 5: Evaluating a Narrow Range of Different Ionization Stabilizing Excipients As described hereinabove, initial screening studies indi-cated that a molar ratio of at least approximately 2-to-1 of sulfuric acid relative to API would be required to stabilize levothyroxine sodium in a DMSO-based solvent system. An additional study was performed to evaluate the range of 2-4x molar ratio (sulfuric acid-to-API) in relatively narrow incre-ments compared to the previously described study.

These studies were performed with a levothyroxine sodium content of 5 mg/mL, corresponding to a molar concentration of approximately 6.25 mM levothyroxine. The acid concentration therefore ranged from 2.0x (12.5 mM) to 4.0x (25.0 mM) and was introduced to the formu-lation through a stock solution of 1N $H_2SO_4$. A statistical software packaged (JMP, v16) was used to develop an experiment containing 24 randomized samples, shown in Table 10.

TABLE 10

Formulation Criteria for Evaluating Narrow Ranges
of $H_2SO_4$ in Levothyroxine Formulations

| Sample No. | Acid Content Molar Ratio (x) | Acid Content (mM) |
|---|---|---|
| 1 | 2.0 | 12.5 |
| 2 | 4.0 | 25.0 |
| 3 | 4.0 | 25.0 |
| 4 | 3.0 | 18.8 |
| 5 | 2.0 | 12.5 |
| 6 | 3.0 | 18.8 |
| 7 | 3.1 | 19.2 |
| 8 | 3.2 | 19.7 |
| 9 | 2.9 | 18.0 |
| 10 | 2.8 | 17.3 |
| 11 | 3.3 | 20.4 |
| 12 | 3.4 | 21.1 |
| 13 | 3.5 | 21.7 |
| 14 | 3.9 | 24.3 |
| 15 | 3.8 | 23.6 |
| 16 | 3.7 | 23.0 |

TABLE 10-continued

Formulation Criteria for Evaluating Narrow Ranges
of $H_2SO_4$ in Levothyroxine Formulations

| Sample No. | Acid Content Molar Ratio (x) | Acid Content (mM) |
|---|---|---|
| 17 | 3.6 | 22.4 |
| 18 | 2.1 | 13.2 |
| 19 | 2.2 | 13.8 |
| 20 | 2.3 | 14.3 |
| 21 | 2.7 | 16.7 |
| 22 | 2.6 | 16.1 |
| 23 | 2.4 | 14.9 |
| 24 | 2.5 | 15.5 |

To maintain a consistent moisture content across all samples (which would otherwise vary based on the volume of 1N $H_2SO_4$ added to each sample), water-for-injection (WFI) was spiked into samples as needed such that the total volume of 1N $H_2SO_4$ plus WFI added to each sample vial was the same across all experimental treatments. No additional formulation excipients were evaluated in this study. Study samples were stored in glass 2R ISO vials (1.0 mL fill volume per vial) at stored in an oven set at 50° C. for seven days and then shifted to 55° C. for an additional 5 days prior to chemical analysis by RP-HPLC.

Figure 22:
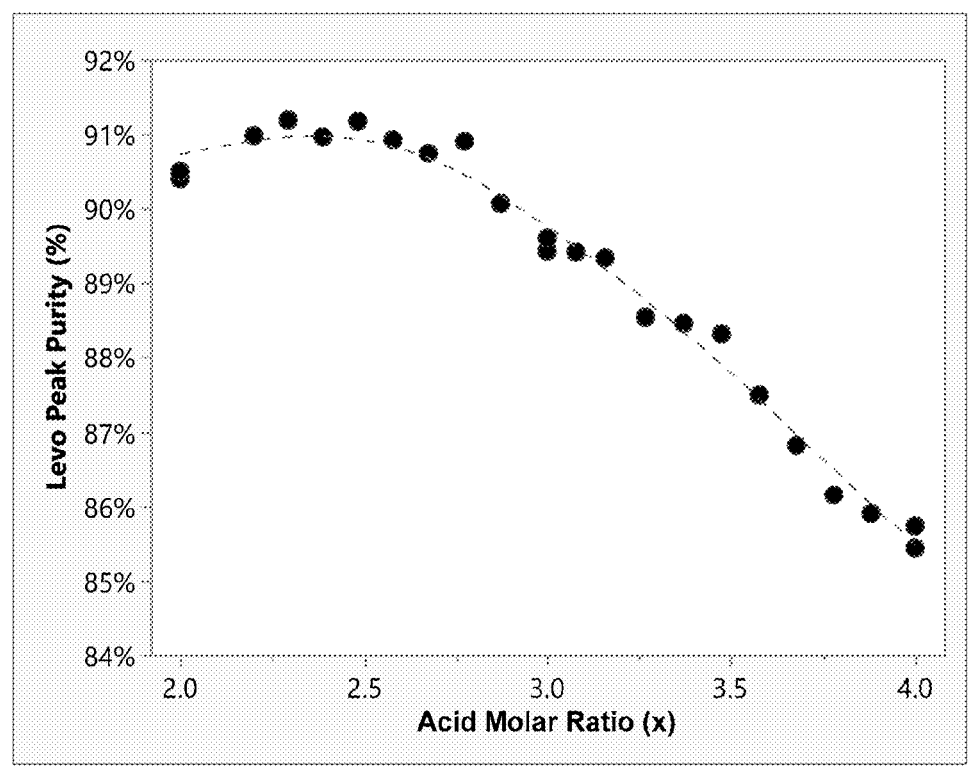
FIG. 22 is a scatter/line graph showing the levothyroxine peak purity of levothyroxine formulations of the invention (measured by RP-HPLC) following 12 days of storage at 50-55° C., as a function of added sulfuric acid content.

In general, the data (presented in FIG. 22 as the percent purity of levothyroxine peak relative to all measured peaks in the chromatogram) indicated a relatively consistent chemical stability of the levothyroxine across a broad range of added sulfuric acid (2.25×-2.75× molar ratio) under the conditions evaluated in this experiment. However, as the acid content was increase to approximately 3.0×, an acid-dependent decline in chemical stability was observed.

All of the embodiments of the present invention, including the compositions and/or methods disclosed and claimed herein, can be made and executed without undue experimentation in light of the present disclosure. While the compositions and methods of this disclosure have been described in terms of certain exemplary embodiments, it will be apparent to those of skill in the art that variations may be applied to the compositions and methods and in the steps or in the sequence of steps of the methods described herein without departing from the concept, spirit, and scope of the disclosure. More specifically, it will be apparent that certain agents, which are both chemically and physiologically related, may be substituted for the agents described herein while the same or similar results would be achieved. All such similar substitutes and modifications apparent to those skilled in the art are deemed to be within the spirit, scope, and concept of any invention as defined by the appended claims.

What is claimed is:

1. A method of treating hypothyroidism in a subject in need thereof, the method comprising introducing into the subject a therapeutically effective amount of a storage stable therapeutic formulation, monitoring levothyroxine levels in the plasma of the subject over time, and repeating the introduction of the therapeutic formulation into the subject as needed to treat hypothyroidism in the subject, wherein the therapeutic formulation comprises:

(a) levothyroxine or a salt thereof, at a concentration of about 10 mg/mL;

(b) an ionization stabilizing excipient, which is sulfuric acid, at a concentration of about 26 mM to about 32 mM;

(c) an aprotic polar solvent, which is dimethyl sulfoxide (DMSO);

(d) a sugar, which is trehalose or a salt or hydrate thereof, at a concentration of about 5.5% (w/v); and (e) a sugar alcohol, which is mannitol, at a concentration of less than 3.0% (w/v);

wherein the therapeutic formulation is storage stable for at least six months at 2° C.-8° C., and wherein the formulation, when administered to the subject, results in the presence of therapeutic levels of levothyroxine in the blood of the subject for an extended period of time relative to an immediate release formulation comprising levothyroxine.

2. The method of claim 1, wherein the levothyroxine or a salt thereof is levothyroxine sodium or levothyroxine free acid.

3. The method of claim 2, wherein the levothyroxine or a salt thereof is levothyroxine sodium.

4. The method of claim 1, wherein the sugar is trehalose dihydrate.

5. The method of claim 1, wherein the therapeutic formulation further comprises a preservative.

6. The method of claim 5, wherein the preservative is a benzyl alcohol.

7. The method of claim 1, wherein the therapeutic formulation is introduced into the subject via parenteral administration.

8. The method of claim 7, wherein the parenteral administration is via injection or infusion.

9. The method of claim 8, wherein the injection is a subcutaneous, intradermal, or intramuscular injection.

10. The method of claim 9, wherein the injection is a subcutaneous injection.

11. The method of claim 8, wherein the infusion is accomplished by pump infusion.

12. The method of claim 11, wherein the pump infusion comprises continuous or bolus pump infusion, or a combination thereof.

13. The method of claim 1, wherein the hypothyroidism is associated with or characterized by thyroiditis, Hashimoto's Disease, myxedema or myxedema coma/crisis.

* * * * *